US006885548B2

(12) United States Patent
Nyberg

(10) Patent No.: US 6,885,548 B2
(45) Date of Patent: Apr. 26, 2005

(54) METHODS OF FABRICATING ANODE LAYERS OF FLAT ELECTROLYTIC CAPACITORS

(75) Inventor: Charles J. Nyberg, Elk River, MN (US)

(73) Assignee: Medtronic, Inc., Minneapolis, MN (US)

( * ) Notice: Subject to any disclaimer, the term of this patent is extended or adjusted under 35 U.S.C. 154(b) by 548 days.

(21) Appl. No.: 10/124,002

(22) Filed: Apr. 17, 2002

(65) Prior Publication Data

US 2003/0199940 A1 Oct. 23, 2003

(51) Int. Cl.[7] .................................................. H01G 9/00
(52) U.S. Cl. ....................... 361/523; 361/528; 361/541; 607/5; 29/25.03
(58) Field of Search ................................. 361/523, 524, 361/528–529, 532, 541; 29/25.03; 607/5

(56) References Cited

U.S. PATENT DOCUMENTS

| | | | |
|---|---|---|---|
| 4,254,775 A | | 3/1981 | Langer |
| 4,942,501 A | | 7/1990 | MacFarlane et al. |
| 5,086,374 A | | 2/1992 | MacFarlane et al. |
| 5,131,388 A | | 7/1992 | Pless et al. |
| 5,146,391 A | | 9/1992 | MacFarlane et al. |
| 5,153,820 A | | 10/1992 | MacFarlane et al. |
| 5,522,851 A | | 6/1996 | Fayram |
| 5,562,801 A | | 10/1996 | Nulty |
| 5,584,890 A | | 12/1996 | MacFarlane et al. |
| 5,628,801 A | | 5/1997 | MacFarlane et al. |
| 5,748,439 A | * | 5/1998 | MacFarlane et al. ........ 361/525 |
| 6,006,133 A | * | 12/1999 | Lessar et al. .................... 607/5 |
| 6,388,866 B1 | * | 5/2002 | Rorvick et al. ............. 361/503 |
| 6,709,946 B1 | * | 3/2004 | O'Phelan et al. ........... 438/396 |

| | | | |
|---|---|---|---|
| 2002/0034062 A1 | | 3/2002 | O'Phelan et al. |

FOREIGN PATENT DOCUMENTS

| | | |
|---|---|---|
| WO | WO00/19470 | 4/2000 |
| WO | WO02/02184 A1 | 1/2002 |
| WO | WO02/02186 A2 | 1/2002 |

OTHER PUBLICATIONS

Karakozov, et al., "Cold Welding Aluminum and Copper Foil, Part 1. Plastic Deformation Process", *Welding International*, 1991 5(4) 300–303.
Troup, "Implantable Cardioverters and Defibrillators", *Current Problems in Cardiology*, vol. XIV, No. 12, Dec. 1989, Chicago.
Lunsmann, "High Energy Density Capacitors for Implantable Defibrillators", presented at CARTS 96: 16th Capacitor and Resistor Technology Symposium Mar. 11–15, 1996.

* cited by examiner

*Primary Examiner*—Anthony Dinkins
(74) *Attorney, Agent, or Firm*—Girma Wolde-Michael; Daniel G. Chapik

(57) ABSTRACT

Implantable medical devices (IMDS) and their various components, including flat electrolytic capacitors for same, and methods of making and using same, particularly an improved electrolytic capacitor. Methods and apparatus for securely mechanically and electrically attaching anode sheets of multi-sheet anode layers of electrolytic capacitors together in a simple manner that does not without unduly damage adjacent or exposed oxide layers are disclosed. The side-by-side stacked multiple anode sheets of a multi-sheet anode layer are joined together by precision cold welding the anode sheets together wherein deformation of the anode sheets is effected by simultaneously driving one or more set of first and second axially aligned cold weld pins into respective first and second stack sides of the stacked anode sheets to substantially equal cold weld depths.

20 Claims, 18 Drawing Sheets

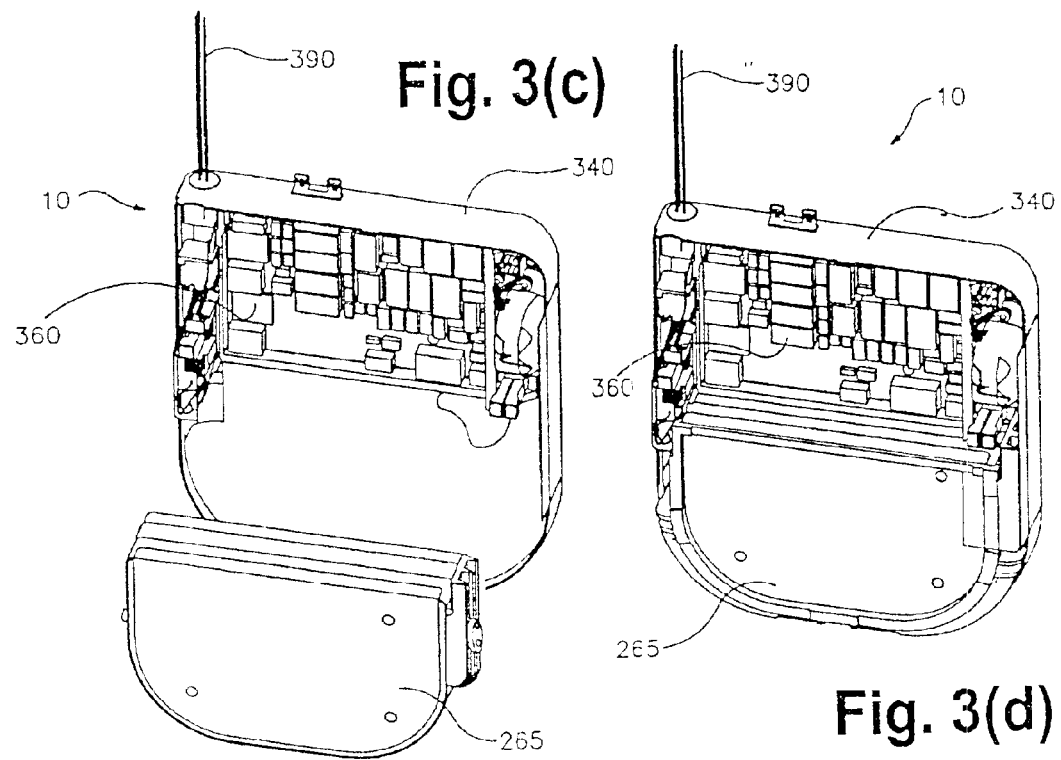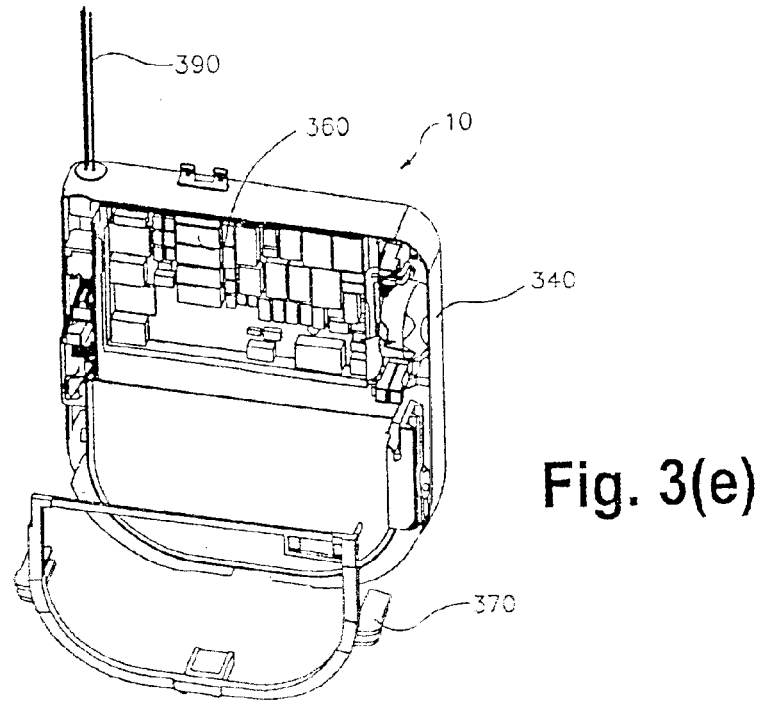

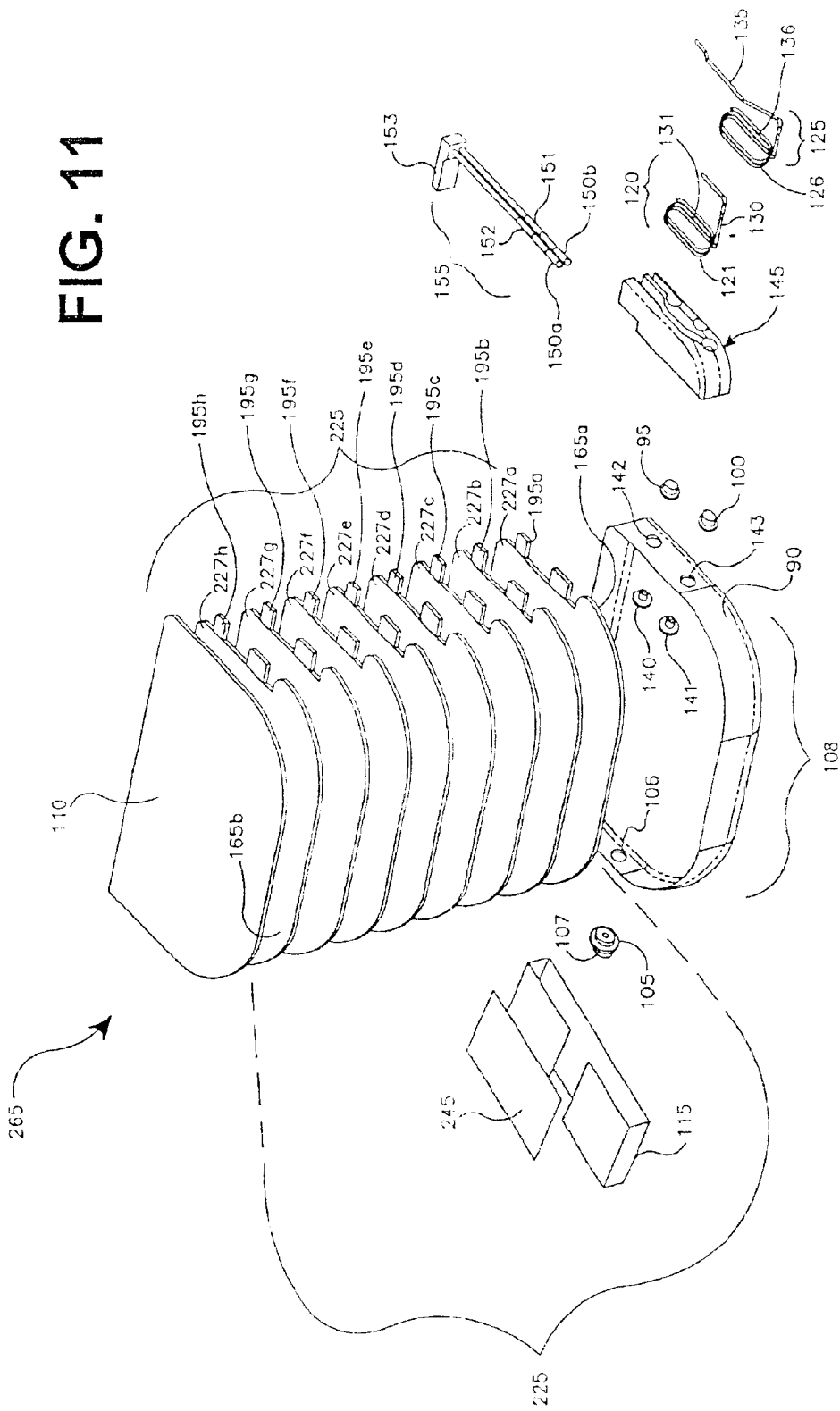

METHODS OF FABRICATING ANODE LAYERS OF FLAT ELECTROLYTIC CAPACITORS

FIELD OF THE INVENTION

This invention relates to implantable medical devices (IMDs) and their various components, including flat electrolytic capacitors for same, and methods of making same, particularly such capacitors fabricated of a plurality of stacked capacitor layers each having anode layers fabricated of a plurality of anodized valve metal anode sheets.

BACKGROUND OF THE INVENTION

A wide variety of IMDs are known in the art. Of particular interest are implantable cardioverter-defibrillators (ICDs) that deliver relatively high-energy cardioversion and/or defibrillation shocks to a patient's heart when a malignant tachyarrhythmia, e.g., atrial or ventricular fibrillation, is detected. The shocks are developed by discharge of one or more high voltage electrolytic capacitor that is charged up from an ICD battery. Current ICDs typically possess single or dual chamber pacing capabilities for treating specified chronic or episodic atrial and/or ventricular bradycardia and tachycardia and were referred to previously as pacemaker/cardioverter/defibrillators (PCDs). Earlier developed automatic implantable defibrillators (AIDs) did not have cardioversion or pacing capabilities. For purposes of the present invention ICDs are understood to encompass all such IMDs having at least high voltage cardioversion and/or defibrillation capabilities.

Energy, volume, thickness and mass are critical features in the design of ICD implantable pulse generators (IPGs) that are coupled to the ICD leads. The battery(s) and high voltage capacitor(s) used to provide and accumulate the energy required for the cardioversion/defibrillation shocks have historically been relatively bulky and expensive. Presently, ICD IPGs typically have a volume of about 40 to about 60 cc, a thickness of about 13 mm to about 16 mm and a mass of approximately 100 grams.

It is desirable to reduce the volume, thickness and mass of such capacitors and ICD IPGs without reducing deliverable energy. Doing so is beneficial to patient comfort and minimizes complications due to erosion of tissue around the ICD IPG. The high voltage capacitor(s) are among the largest components that must be enclosed within the ICD IPG housing. Reductions in size of the capacitors may also allow for the balanced addition of volume to the battery, thereby increasing longevity of the ICD IPG, or balanced addition of new components, thereby adding functionality to the ICD IPG. It is also desirable to provide such ICD IPGs at low cost while retaining the highest level of performance. At the same time, reliability of the capacitors cannot be compromised.

Various types of flat and spiral-wound capacitors are known in the art, some examples of which are described as follows and/or may be found in the patents listed in Table 1 of commonly assigned U.S. Pat. No. 6,006,133. Typically, an electrolytic capacitor is fabricated with a capacitor case enclosing a "valve metal" (e.g., aluminum) anode layer (or "electrode"), a valve metal (e.g. aluminum) cathode layer (or "electrode"), and a Kraft paper or fabric gauze spacer or separator impregnated with a solvent based liquid electrolyte interposed therebetween. The aluminum anode layer is typically fabricated from aluminium foil that is first etched and then "formed" by passage of electrical current through the anode layer to oxidize the etched surfaces so that the aluminium oxide functions as a dielectric layer. The electrolyte comprises an ion producing salt that is dissolved in a solvent and provides ionic electrical conductivity between the cathode layer and the aluminum oxide dielectric layer. The energy of the capacitor is stored in the electromagnetic field generated by opposing electrical charges separated by the aluminum oxide layer disposed on the surface of the anode layer and is proportional to the surface area of the etched aluminum anode layer. Thus, to minimize the overall volume of the capacitor one must maximize anode surface area per unit volume without increasing the capacitor's overall (i.e., external) dimensions. The separator material, anode and cathode layer terminals, internal packaging, electrical interconnections, and alignment features and cathode material further increase the thickness and volume of a capacitor. Consequently, these and other components in a capacitor and the desired capacitance limit the extent to which its physical dimensions may be reduced.

Some ICD IPGs employ commercial photoflash capacitors similar to those described by Troup in "Implantable Cardioverters and Defibrillators," *Current Problems in Cardiology*, Volume XIV, Number 12, Dec. 1989, Year Book Medical Publishers, Chicago, and as described in U.S. Pat. No. 4,254,775. The electrodes or anode and cathodes are wound into anode and cathode layers separated by separator layers of the spiral. Most commercial photoflash capacitors contain a core of separator paper intended to prevent brittle, highly etched aluminum anode foils from fracturing during winding of the anode, cathode, and separator layers into a coiled configuration. The cylindrical shape and paper core of commercial photoflash capacitors limits the volumetric packaging efficiency and thickness of an ICD IPG housing made using same.

More recently developed ICD IPGs employ one or more flat or "prismatic", high voltage, electrolytic capacitor to overcome some of the packaging and volume disadvantages associated with cylindrical photoflash capacitors. Flat aluminum electrolytic capacitors for use in ICD IPGs have been disclosed, e.g., those improvements described in "High Energy Density Capacitors for Implantable Defibrillators" presented by P. Lunsmann and D. MacFarlane at *CARTS 96: 16th Capacitor and Resistor Technology Symposium*, 11–15 Mar. 1996, and at *CARTS-EUROPE 96: 10th European Passive Components Symposium.*, 7–11 Oct. 1996, pp. 35–39. Further features of flat electrolytic capacitors for use in ICD IPGs are disclosed in U.S. Pat. Nos. 4,942,501; 5,086,374; 5,131,388; 5,146,391; 5,153,820; 5,522,851, 5,562,801; 5,628,801; and 5,748,439, all issued to MacFarlane et al.

For example, U.S. Pat. Nos. 5,131,388 and 5,522,851 disclose a flat capacitor having a plurality of stacked capacitor layers each comprising an "electrode stack subassembly". Each capacitor layer contains one or more anode sheet forming an anode layer having an anode tab, a cathode sheet or layer having a cathode tab and a separator for separating the anode layer from the cathode layer.

Electrical performance of such electrolytic capacitors is effected by the surface area of the anode and cathode layers and also by the resistance associated with the electrolytic capacitor itself, called the equivalent series resistance (ESR). The ESR is a "hypothetical" series resistance that represents all energy losses of an electrolytic capacitor regardless of source. The ESR results in a longer charge time (or larger build factor) and a lower discharge efficiency. Therefore, it is desirable to reduce the ESR to a minimum.

Typically, ESR is minimized by fabricating the anode layer of each capacitor layer from highly etched valve metal foil, e.g., aluminum foil, that has a microscopically contoured, etched surface with a high concentration of pores extending part way through the anode foil along with tunnels extending all the way through the anode foil (through-etched or tunnel-etched) or only with a high concentration of pores extending part way through the anode foil (nonthrough-etched). In either case, such a through-etched or nonthrough-etched anode sheet cut from such highly etched foil exhibit a total surface area much greater than its nominal (length times width) surface area. A surface area coefficient, the ratio of the microscopic true surface area to the macroscopic nominal area, may be as high as 100:1, which advantageously increases capacitance. Through-etched or tunnel-etched anode sheets exhibit a somewhat lower ratio due to the absence of a web or barrier surface closing the tunnel as in nonthrough-etched anode sheets.

After the aluminum foil is etched, the aluminum oxide layer on the etched surface is "formed" by applying voltage to the foil through an electrolyte such as boric acid or citric acid and water or other solutions familiar to those skilled in the state of the art. Typically, individual anode sheets are punched, stamped or otherwise cut out of the foil in a shape to conform to the capacitor package following formation of the aluminum oxide on the foil. The cut edges around the periphery of the anode sheets are carefully cleaned to remove particulates of anode material that can get caught between the capacitor layers in the electrode stack assembly resulting in a high leakage current or capacitor failure. Anode layers comprise either a single anode sheet or multiple anode sheets. Capacitor layers are assembled by stacking the anode layer, separator layers, and cathode layer together, and electrode stack assemblies are assembled by stacking a plurality of capacitor layers together, separated by separator layers. The cut edges of the anode and cathode layers and any other exposed aluminum are then reformed in the capacitor during the aging process to reduce leakage current.

In order to increase capacitance (and energy density), multiple anode sheets are stacked together to form the multiple sheet anode layer as described above. Through-etched or tunnel-etched anode sheets need to be used in such multiple sheet anode layers to ensure that electrolyte is distributed over all of the aluminum oxide layers of the sandwiched inner anode sheets and to provide a path for ionic communication. But, then the gain in surface area is not as high as that which can be achieved with a like number of stacked non-through-etched anode sheets that have a remaining solid section in their center.

For example, the '890 patent discloses the use of an anode layer fabricated from a highly etched center sheet with a solid core and two tunnel-etched anode sheets sandwiching the center sheet. This arrangement is intended to allow the electrolyte, and thus the conducting ions, to reach all surface areas of the three sheet anode layer while preventing the ions from passing all the way through the anode layer. More than three tunnel etched anode sheets can be used in the anode layer depending on the desired electrical performance.

The aluminum oxide layers electrically isolate the aluminum sheets of the aluminum layer from each other, and an electrical connection must be made between the underlying aluminum valve metal of each anode sheet of the anode layer. In one approach, each anode sheet of each anode layer is fabricated with an outwardly projecting anode tab. The tabs of the anode layers and the cathode layers of all of the capacitor layers of the stack are electrically connected in parallel to form a single capacitor or grouped to form a plurality of capacitors. The attached aluminum anode sheet tabs are electrically connected to a feedthrough pin of an anode feedthrough extending through the case or compartment wall. In the above-referenced '851 patent, each of the anode sheet tabs are welded together and then welded to a post of a feedthrough pin. The single sheet cathode layers are also fabricated with cathode tabs that are also gathered together and electrically connected to a feedthrough pin of a cathode feedthrough extending through the case or compartment wall or connected to the electrically conductive capacitor case wall.

Capacitor volume can be reduced slightly by interposing and welding a shared anode tab in between two adjacent anode sheets in the anode stack, as described, for example, in the above-referenced '388 patent. No particular method of welding is disclosed, and the interposed stack of anode tabs would thicken and distort the anode sheet stack making it difficult to fit into a flat sided capacitor housing.

In another approach described in U.S. Pat. No. 5,584,890, the center anode sheet of a three sheet anode layer is fabricated with an inward recess into which an anode tab is inserted. The three anode sheets are joined together at a distance from the anode tab by using cold welding, although laser welding and arc welding are mentioned as alternatives without detail.

In the above-referenced '133 patent, a single anode tab is fitted into a slot of one of the stacked anode sheets and attached to one or more of the adjoining anode sheets by cold welding. The anode sheets are cold welded together at more than one location by use of a press and press fixture having spring-loaded or pneumatically driven cold weld pins that extend through pin bores of a top plate and a base plate bearing against the uppermost and lowermost exposed surfaces of the stack of anode sheets to be cold welded together.

By necessity, the joinder of anode sheets together to form multi-sheet anode layers and to separate anode tabs by such techniques must break through the oxide layer over the exposed etched surfaces of the anode sheets and fill or compress the underlying etched surface until the valve metals of the sheet cores are in intimate contact such that a low resistance electrical connection is achieved. Typically, it is necessary to provide multiple attachment sites to provide redundancy, which increases reliability. But breaking through the etched oxide layers of the multiple sheets in multiple places reduces the overall capacitance. Moreover, the attachment techniques can damage the etched oxide layers adjacent to the points of attachment or across the exposed outermost anodized surfaces of the outermost sheets of the anode layer.

In the '133 patent, the spring loaded or pneumatically driven axially aligned cold weld pins are advanced like pistons out of pin cylinders in upper and lower plates into the respective upper and lower stack sides of the anode sheet stack positioned between them. The opposed cold weld pins are intended to be in axial alignment and therefore in registration to press depressions into both of the upper and lower stack sides that cold weld the anode sheets by mechanical compression of the anode sheet layers. The opposed cold weld pins can be driven to unequal depths in the opposed stack sides. The cold weld pins can become misaligned or out of registration as the cold weld pins of the pin cylinders wear, resulting in misaligned cold weld depressions into the opposed stack sides. The quality of the cold welds can therefore suffer unless rigorous inspection procedures of the cold weld pins and the resulting assembled anode layers are carried out.

Thus, there is a need for further reducing capacitor volume, increasing capacitor reliability, and reducing cost and complexity of the capacitor manufacturing process, for multi-sheet anode layers in capacitors used in ICDs and other IMDs and other electric circuit applications.

SUMMARY OF THE INVENTION

The present invention provides for methods and apparatus for securely mechanically and electrically attaching anode sheets of multi-sheet anode layers of electrolytic capacitors together in a simple manner that does not without unduly damage adjacent or exposed oxide layers.

In accordance with the present invention, the side-by-side stacked multiple anode sheets of a multi-sheet anode layer are joined together by precision cold welding the anode sheets together wherein deformation of the anode sheets is effected by simultaneously driving one or more set of first and second axially aligned cold weld pins into respective first and second stack sides of the stacked anode sheets to substantially equal cold weld depths. The interposed anode sheets are compressed substantially together so that the etched and oxidized layers overlying each core layer are crushed and intermingled with the core layer valve metal to make an electrical connection between the anode sheets. In this way, uniformly sized and strong cold welds of all of the anode sheets are achieved while minimizing damage to adjoining oxide layers of the anode sheets so that capacitance per unit area is maximized.

The method of the invention is preferably also employed to fix an anode tab to the anode sheets of the anode layer. At least one anode sheet is cut to a shape having a slot or notch into which a portion of the anode tab is fitted. The remaining anode sheets are shaped to overly the portion of the anode tab. First and second axially aligned cold weld pins are driven into the first and second stack sides of the stacked anode sheets to weld the anode sheets other than the anode sheet with the notch receiving the anode tab portion with the anode tab.

The cold welding is effected through the use of a horizontal or vertical press and fixture that applies minimal forces against the first and second stack sides an anode sheet stack while driving the axially aligned and opposed cold weld pins toward one another with substantially equal opposed forces and to substantially equal cold weld depths. The press fixture comprises a first plate assembly and a second plate assembly arranged to receive the anode sheet stack supported between the first and second plate assemblies. The first and second plate assemblies each support one or preferably a plurality of cold weld dies each having a cold weld pin such that the cold weld pins extend outward and toward the first and second stack sides of the anode sheet stack in substantially axial alignment with one another. The first and second plate assemblies are brought together toward the first and second stack sides, and each cold weld pin presses into the interposed anode sheet stack to a cold weld depth (CWD). The press fixture or the first and second plate assemblies preferably include registration pins or a registration frame for maintaining the anode sheets as well as the anode tab aligned in the anode sheet stack.

The first plate assembly comprises one or preferably a plurality of first cold weld dies each having a cold weld pin extending from a cold weld die body such that the cold weld pins extend toward the first stack side of the anode sheet stack and a first force plate that bears against all of the first cold weld die bodies. Similarly, the second plate assembly comprises one or preferably a like plurality of second cold weld dies each having a cold weld pin extending from a cold weld die body such that the cold weld pins extend toward the second stack side of the anode sheet stack and a second force plate that bears against all of the second cold weld die bodies. The force of the press is distributed equally to all of the first and second cold weld dies through the respective first and second force plates.

The first and second cold weld dies can be fabricated integrally with the respective first and second force plate such that the cold weld die bodies are integrally subsumed into the cold weld plates and the cold weld pins extend from the force plates by a cold weld pin length that is correlated to the CWD. Preferably, the single ones or pluralities of first and cold weld dies are separate from the first and second force plates so that the single ones or pluralities of first and cold weld dies can be replaced as the cold weld pins wear out through use.

In one approach, the cold weld die bodies of a plurality of first and second cold weld dies can be joined together as first and second unitary cold weld dies each thereby having a unitary cold weld body that is substantially planar and integrally supports the cold weld pins extending from the substantially planar body surface by a cold weld pin length that is correlated to the CWD.

In a preferred embodiment, first and second like pluralities of cold weld dies are fabricated with die bodies that fit or plug into die body receptacles of respective first and second substantially planar die holders. The cold weld pins extend outward from the first and second die holder and toward the respective first and second stack sides of the anode sheet stack while the die bodies are held in the die body receptacles of the die holders.

The cold weld pins extending from the cold weld die bodies remain in axial alignment because the cold weld die bodies do not move with respect to the die body receptacles whereby wear of the die body receptacles and the die bodies is eliminated.

One or both of the first and second plate assemblies optionally include CWD stop members that limit the CWD achieved by each cold weld pin. In effect, the advancement of the cold weld pins is stopped when the first and second plate assemblies come into contact with one another. Or the CWD is regulated by feedback of measured applied force such that the advancement of the first and second plate assemblies is halted when a predetermined applied force is measured. Or the CWD is regulated by presetting the press limit advancement of the first and second plate assemblies to a fixed distance.

The cold weld pins have a relatively small pin cross section area relative to the area of the first and second stack sides of the anode sheet stack. Therefore, the force required to press the cold weld pins into the anode sheet stack from the first and second stack sides in substantially axially alignment is considerably less than the force required to compress the anode sheet stack as a whole. Therefore, if the applied force is limited, the anode sheet stack can itself constitute a CWD stop that is operative when the substantially planar surfaces of the substantially planar die holders or integral die bodies or force plates contact the first and second outermost surfaces. In this way, the final separation apart of the first and second plate assemblies is substantially equal to the sheet stack height (SSH). And, the CWD in each instance is substantially equal to the cold weld pin length extending from the substantially planar surface of the die holders or integral die bodies or force plates.

In a vertical press, the first and second plate assemblies are referred to as upper and lower plate assemblies, respectively, situated above the first or upper stack side and the second or lower stack side, respectively, of the horizontally stacked anode sheets of the anode layer to be fabricated. In one preferred embodiment in this context, the upper plate assembly comprises an upper die holder that preferably holds a plurality of upper cold weld dies each having an upper cold weld pin extending downward from an upper die body such that the cold weld pins extend outward and downward from the upper die holder and toward the upper stack side of the anode sheet stack. An upper force plate is positioned above the upper die holder to apply equal force and displacement against the upper die holder and the upper die bodies held by the upper die holder. Similarly, the lower plate assembly comprises a lower die holder that holds a plurality of lower cold weld dies each having a lower cold weld pin extending upward from a lower die body such that the cold weld pins extend outward and upward from the lower die holder and toward the lower stack side of the anode sheet stack. A lower force plate is positioned below the lower die holder to apply equal force and displacement against the lower die holder and the lower die bodies held by the lower die holder. The lower plate assembly is preferably supported in a press bed, whereby the lower stack side of the anode sheet stack rests upon the lower cold weld pins and are maintained in registration. The upper plate assembly is preferably suspended on a movable press arm that is brought down against the upper stack side of the anode sheet stack until the prescribed CWD is achieved by each cold weld pin.

A capacitor is assembled from the anode layer, a cathode layer, and a separator between the anode layer and the cathode and fitted into a capacitor case with appropriate electrical connectors to the anode and cathode layers. Or, a capacitor layer is assembled from the anode layer, a cathode layer, and a separator between the anode layer and the cathode, and a plurality of the cathode layers are stacked into a capacitor sub-assembly, electrically interconnected and fitted into a capacitor case with appropriate electrical connectors to the anode and cathode layers.

In one embodiment, an exemplary electrolytic capacitor fabricated in accordance with the present invention comprises an electrode stack assembly and electrolyte located within the interior case chamber of a hermetically sealed capacitor case. The electrode stack assembly comprises a plurality of capacitor layers stacked in registration upon one another, each capacitor layer comprising a cathode layer having a cathode tab, an anode layer comprising at least one anode sheet having an anode tab, and a separator layer located between adjacent anode and cathode layers, whereby all adjacent cathode layers and anode layers of the stack are electrically insulated from one another by a separator layer. Anode terminal means extend through the capacitor case side wall for electrically connecting a plurality of the anode tabs to one another and providing an anode connection terminal at the exterior of the case. Cathode terminal means extend through or to an encapsulation area of the capacitor case side wall for electrically connecting a plurality of the cathode tabs to one another and providing a cathode connection terminal at the exterior of the case. A connector assembly is electrically attached to the anode connection terminal for making electrical connection with the anode tabs and to the cathode connection terminal for making electrical connection with the cathode tabs.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other aspects and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 11 is an exploded top perspective view of one embodiment of a series of capacitor layers each incorporating the anode layers of the present invention ready to be assembled into a electrode stack assembly and fitted together with the remaining components of one embodiment of an electrolytic capacitor;

DETAILED DESCRIPTION OF THE PREFERRED EMBODIMENTS

A preferred embodiment of the present invention is described herein in relation to an ICD IPG without limitation as to other uses of electrolytic capacitors fabricated in accordance with the general principles of the invention. The following described capacitor and ICD takes the overall form of those disclosed in the above-referenced, commonly assigned '133 and related patents, but the present invention can be employed in the fabrication of electrolytic capacitors of any configuration used in ICDs, other IMDs and in other applications. While the present invention can be practiced using valve metals of any type, aluminum is employed in the preferred embodiments described herein.

Figure 1:
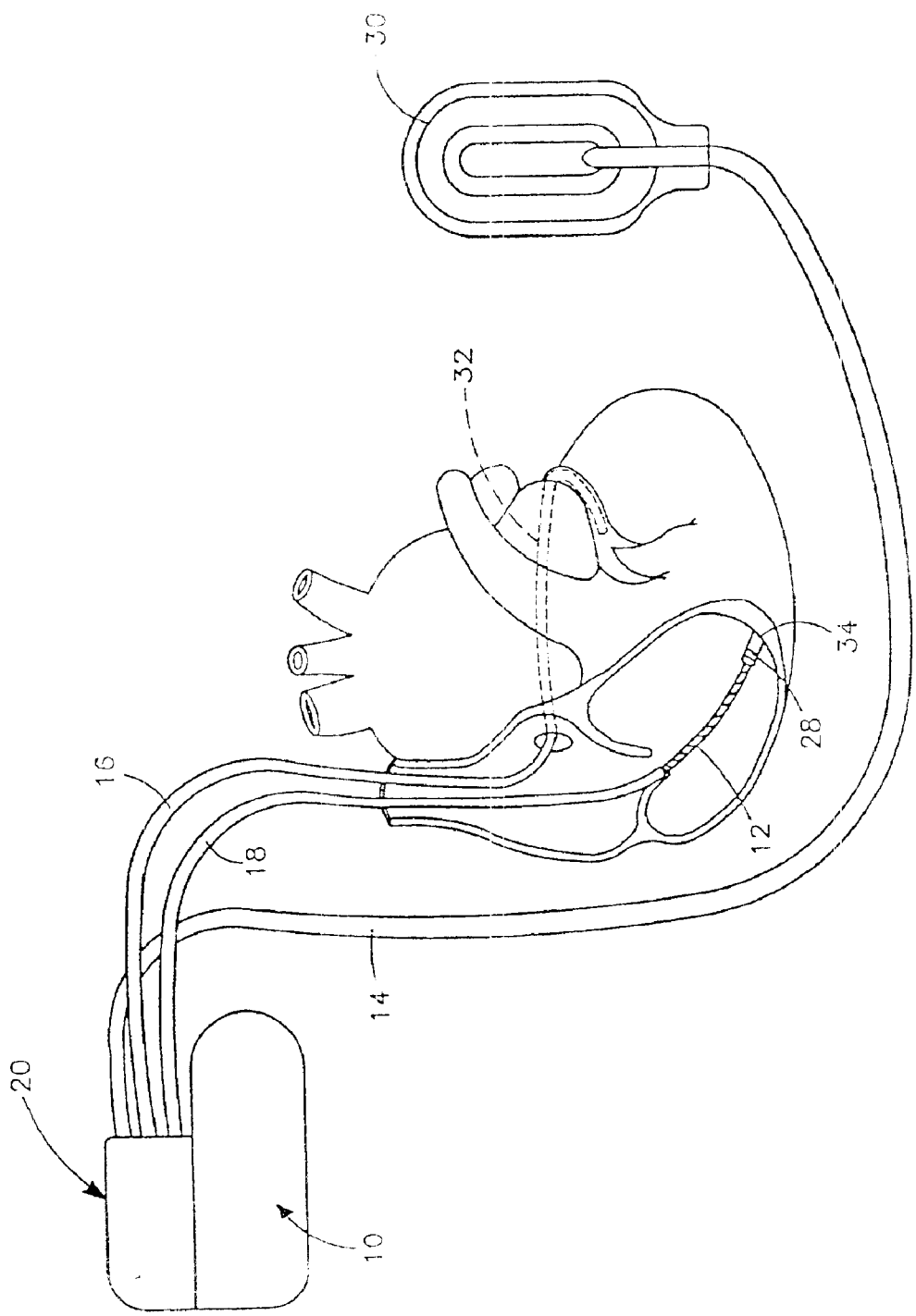
FIG. 1 illustrates the physical components of one exemplary embodiment of an ICD IPG and lead system in which the present invention may be advantageously incorporated.

FIG. 1 illustrates one embodiment of ICD IPG 10 in which the capacitor of the present invention is advantageously incorporated, the associated ICD electrical leads 14, 16 and 18, and their relationship to a human heart 12. The leads are coupled to ICD IPG 10 by means of multi-port connector block 20, which contains separate connector ports for each of the three leads illustrated. Lead 14 is coupled to subcutaneous electrode 30, which is intended to be mounted subcutaneously in the region of the left chest. Lead 16 is a coronary sinus lead employing an elongated coil electrode that is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with elongated electrode coil 28 that is located in the right ventricle of the heart. Lead 18 also includes stimulation electrode 34 that takes the form of a helical coil that is screwed into the myocardial tissue of the right ventricle. Lead 18 may also include one or more additional electrodes for near and far field electrogram sensing.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32. During sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation shock regimens may be also provided, typically between electrode 28 and coronary sinus electrode 32. Alternatively, single pulses may be delivered between electrodes 28 and 30. The particular interconnection of the electrodes to an ICD will depend somewhat on which specific single electrode pair defibrillation shock regimen is believed more likely to be employed.

Figure 2:
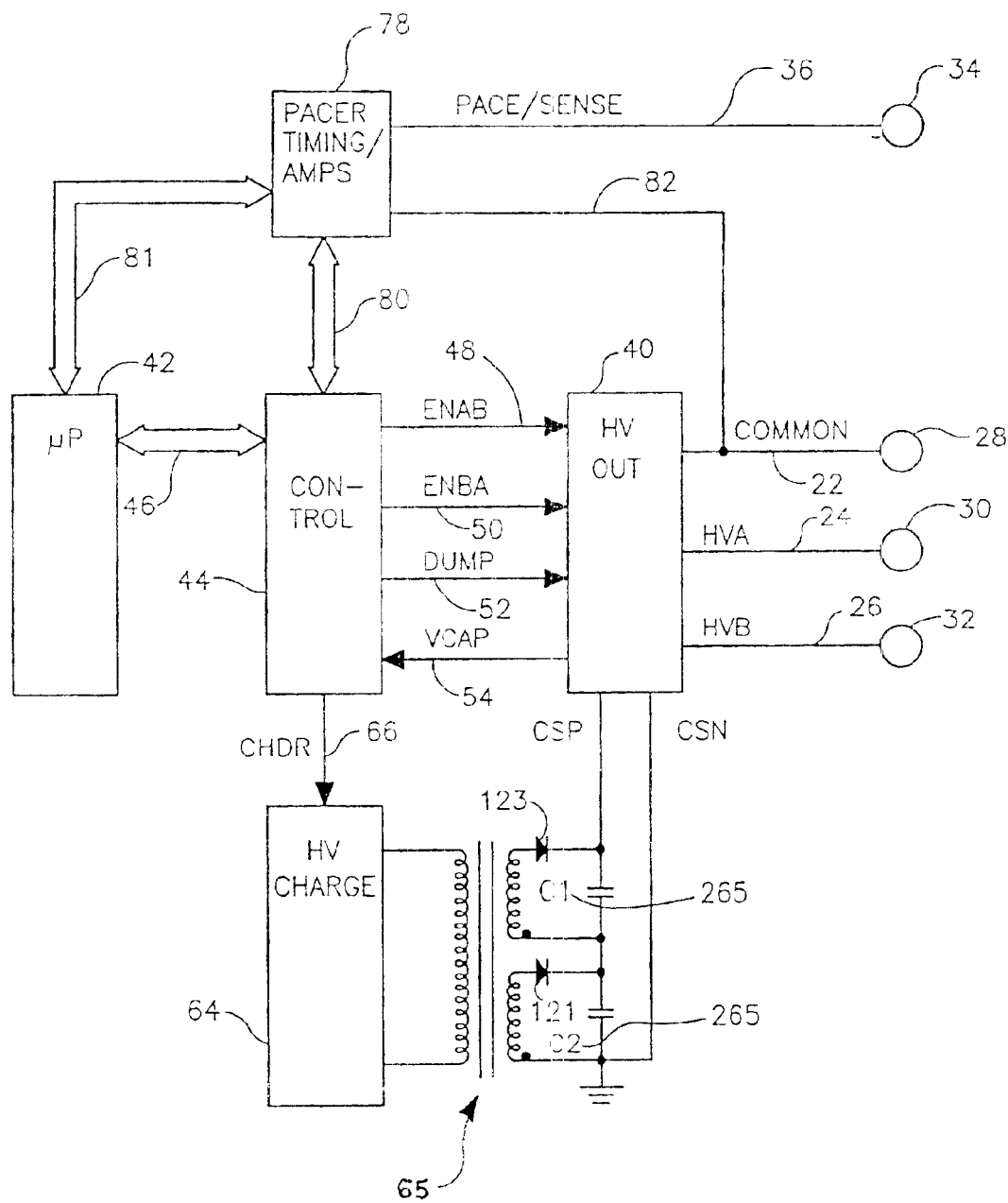
FIG. 2 is a simplified functional block diagram illustrating the interconnection of voltage conversion circuitry with the high voltage capacitors of the present invention with the primary functional components of one type of an ICD.
Figure 3A:
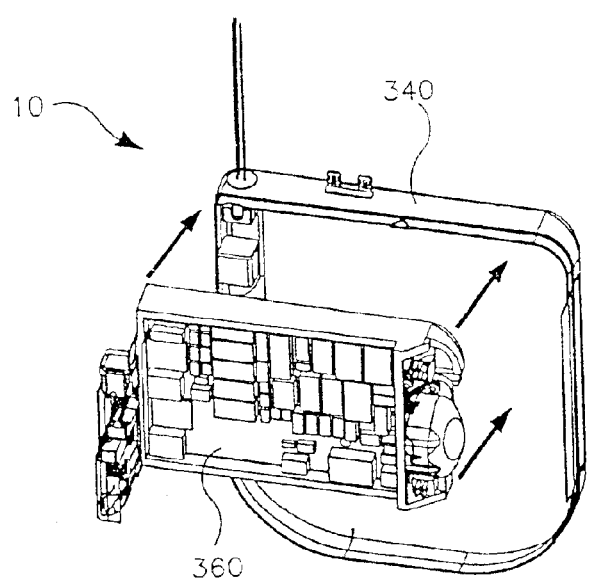
FIGS. 3($a$)–3($g$) are exploded perspective views of the manner in which the various components of the exemplary ICD IPG of FIGS. 1 and 2, including the electrolytic capacitors of the present invention, are disposed within the housing of the ICD IPG.
Figure 3B:
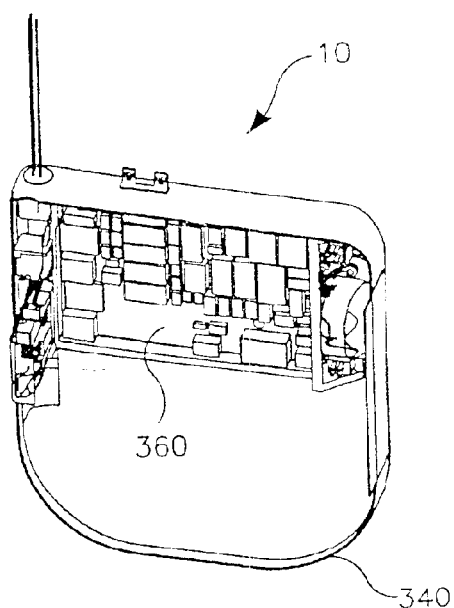
Figure 3F:
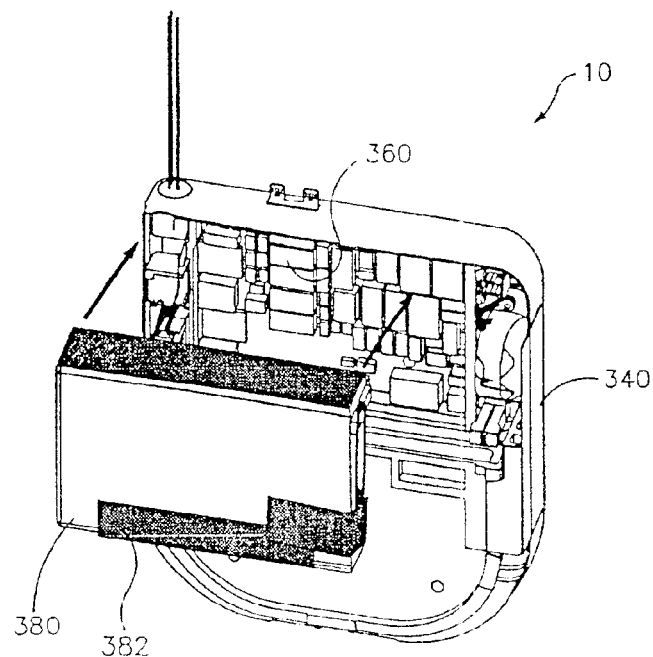
Figure 3G:
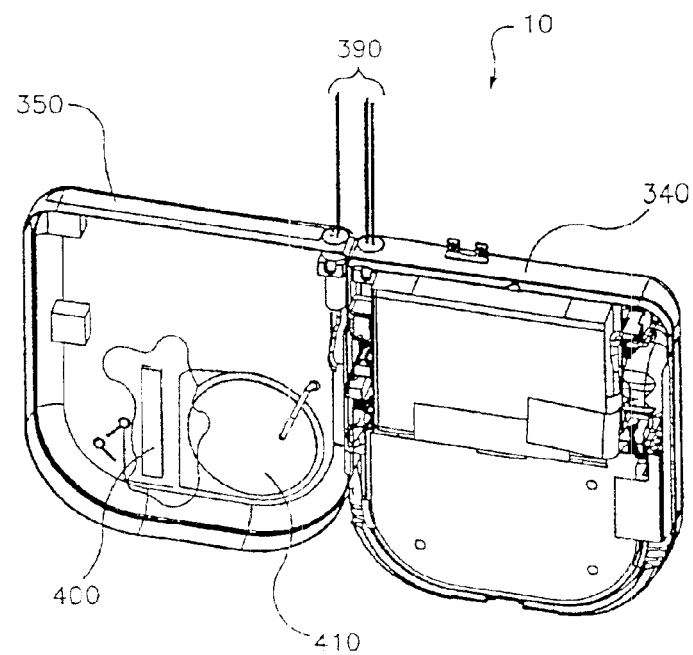

FIG. 2 is a block diagram illustrating the interconnection of high voltage output circuit 40, high voltage charging circuit 64 and capacitors 265 according to one example of the microcomputer based operating system of the ICD IPG of FIG. 1. As illustrated, the ICD operations are controlled by means of a stored program in microprocessor 42, which performs all necessary computational functions within the ICD. Microprocessor 42 is linked to control circuitry 44 by means of bi-directional data/control bus 46, and thereby controls operation of the output circuitry 40 and the high voltage charging circuitry 64. Pace/sense circuitry 78 awakens microprocessor 42 to perform any necessary mathematical calculations, to perform tachycardia and fibrillation detection procedures and to update the time intervals controlled by the timers in pace/sense circuitry 78 on reprogramming of the ICD operating modes or parameter values or on the occurrence of signals indicative of delivery of cardiac pacing pulses or of the occurrence of cardiac contractions,.

The basic operation and particular structure or components of the exemplary ICD of FIGS. 1 and 2 may correspond to any of the systems known in the art, and the present invention is not dependent upon any particular configuration thereof. The flat aluminum electrolytic capacitor of the present invention may be employed generally in conjunction with the various systems illustrated in the aforementioned '209 patent, or in conjunction with the various systems or components disclosed in the various patents listed in the above-referenced '133 patent.

Control circuitry 44 provides three signals of primary importance to output circuitry 40. Those signals include the first and second control signals discussed above, labelled here as ENAB, line 48, and ENBA, line 50. Also of importance is DUMP line 52 that initiates discharge of the output capacitors and VCAP line 54 that provides a signal indicative of the voltage stored on the output capacitors C1, C2, to control circuitry 44. Defibrillation electrodes 28, 30 and 32 illustrated in FIG. 1, above, are shown coupled to output circuitry 40 by means of conductors 22, 24 and 26. For ease of understanding, those conductors are also labelled as "COMMON", "HVA" and "HVB". However, other configurations are also possible. For example, subcutaneous electrode 30 may be coupled to HVB conductor 26, to allow for a single pulse regimen to be delivered between electrodes 28 and 30. During a logic signal on ENAB, line 48, a cardioversion/defibrillation shock is delivered between electrode 30 and electrode 28. During a logic signal on ENBA, line 50, a cardioversion/defibrillation shock is delivered between electrode 32 and electrode 28.

The output circuitry includes a capacitor bank, including capacitors C1 and C2 and diodes 121 and 123, used for delivering defibrillation shocks to the electrodes. Alternatively, the capacitor bank may include a further set of capacitors as depicted in the above referenced '758 application. In FIG. 2, capacitors 265 are illustrated in conjunction with high voltage charging circuitry 64, controlled by the control/timing circuitry 44 by means of CHDR line 66. As illustrated, capacitors 265 are charged by means of a high frequency, high voltage transformer 65. Proper charging polarities are maintained by means of the diodes 121 and 123. VCAP line 54 provides a signal indicative of the voltage on the capacitor bank, and allows for control of the high voltage charging circuitry and for termination of the charging function when the measured voltage equals the programmed charging level.

Pace/sense circuitry 78 includes an R-wave sense amplifier and a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 80.

Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 illustrated in FIG. 1 by means of a conductor 36. Pace/sense circuitry 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

FIGS. 3(*a*) through 3(*g*) show perspective views of various components of ICD IPG 10, including one embodiment of the capacitor of the present invention, as those components are placed successively within the housing of ICD IPG 10 fabricated by right and left hand shields 240 and 350.

In FIG. 3(*a*), electronics module 360 is placed in right-hand shield 340 of ICD IPG 10. FIG. 3(*b*) shows ICD IPG 10 once electronics module 360 has been seated in right-hand shield 340.

FIG. 3(*c*) shows a pair of capacitors 265 fabricated as described herein prior to being placed within right-hand shield 340, the capacitors 265 being connected electrically in series by interconnections in electronics module 340. FIG. 3(*d*) shows ICD IPG 10 once the pair of capacitors 265 has been placed within right-hand shield 340. It will be understood that other shapes of capacitors 265 can be inserted into the housing of ICD IPG 10 in the same or similar manner as described here.

FIG. 3(*e*) shows insulator cup 370 prior to its placing atop capacitors 265 in right-hand shield 340. FIG. 3(*f*) shows electrochemical cell or battery 380 having insulator 382 disposed around battery 380 prior to placing it in shield 340. Battery 380 provides the electrical energy required to charge and re-charge capacitors 265, and also powers electronics module 360. Battery 380 may take any of the forms employed in the prior art to provide cardioversion/defibrillation energy, some of which are identified in above referenced, commonly assigned, '133 patent.

FIG. 3(*g*) shows ICD IPG 10 having left-hand shield 350 connected to right-hand shield 340 and feedthrough 390 projecting upwardly from both shield halves. Activity sensor 400 and patient alert apparatus 410 are shown disposed on the side lower portion of left-hand shield 350. Left-hand shield 350 and right-hand shield 340 are subsequently closed and hermetically sealed (not shown in the figures).

Figure 4:
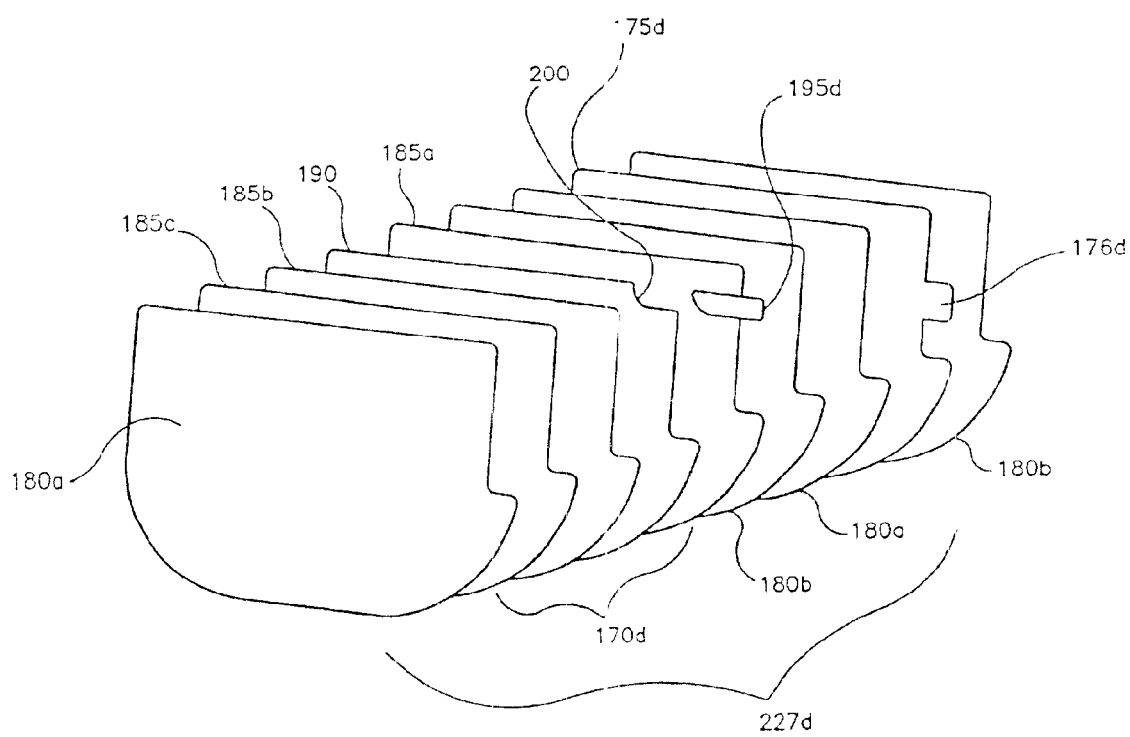
FIG. 4 is an exploded view of one embodiment of a single capacitor layer of an electrolytic capacitor incorporating the present invention.

FIG. 4 shows an exploded view of one embodiment of an anode-cathode sub-assembly or capacitor layer 227 of capacitor 265 in which the present invention may be implemented. It will be understood that the teachings of the present invention can be employed in the fabrication of and in the resulting capacitors employing a single cathode layer, a single anode layer formed of a plurality of anode sheets assembled together and to an anode tab as described herein, and a separator separating the anode layer and cathode layer.

The exemplary capacitor design described herein employs a stacked configuration of a plurality of capacitor layers 227 as further described below with respect to FIG. 5. Each capacitor layer 227 comprises alternating substantially rectangular-shaped anode layers 170 and cathode layers 175, with a substantially rectangular-shaped separator layer 180 being interposed therebetween. The shapes of anode layers 170, cathode layers 175 and separator layers 180 are primarily a matter of design choice, and are dictated largely by the shape or configuration of case 90 within which those layers are ultimately disposed. Anode layers 170, cathode layers 175 and separator layers 180 may assume any arbitrary shape to optimize packaging efficiency.

The exemplary anode layer 170*d* shown in FIG. 4 most preferably comprises a plurality of non-notched anode sheets 185 designated 185*a*, 185*b*, 185*c* and notched anode sheet 190, including anode tab notch 200, that are to be cold welded together in accordance with the present invention, and anode tab 195 that is to be cold welded to anode sheets 185*a*, 185*b*, and 185*c* in accordance with the present invention. It will be understood that anode layer 170*d* shown in FIG. 4 is but one possible embodiment of an anode layer 170. Exemplary cathode layer 175*d* most preferably is fabricated of a single sheet of aluminum foil and has cathode tab 176 fabricated integral thereto and projecting from the periphery thereof.

Individual anode sheets 185*a*, 185*b*, 190 and 185*c* (alternatively referred to as anode sheets 185/190 herein) are cut from high-purity aluminum foil formed as described above to achieve high capacitance per unit area. Thin anode sheets 185/190 are preferred, especially if they substantially maintain or increase specific capacitance while reducing the thickness of the electrode stack assembly 225, or maintain the thickness of electrode stack assembly 225 while increasing overall capacitance. For example, it is contemplated that individual anode sheets 185/190 have a thickness of between about 10 micrometers and about 500 micrometers.

Cathode layer 175 is preferably a single cathode sheet cut from high purity, flexible, aluminum foil. Cathode layer 175 is most preferably cut from aluminum foil having high surface area (i.e., highly etched cathode foil), high specific capacitance (preferably at least 200 microfarads/cm$^2$, and at least 250 microfarads/cm$^2$ when fresh), a thickness of about 30 micrometers, a cleanliness of about 1.0 mg/m$^2$ respecting projected area maximum chloride contamination, and a purity which may be less than corresponding to the starting foil material from which anode foil is made. The cathode foil preferably has an initial purity of at least 99% aluminum, and more preferably yet of about 99.4% aluminum, a final thickness of about 30 micrometers, and an initial specific capacitance of about 250 microfarads per square centimeter. In other embodiments, cathode foil has a specific capacitance ranging between about 100 and about 500 microfarads/cm$^2$, and a thickness ranging between about 10 and about 150 micrometers.

It is generally preferred that the specific capacitance of the cathode foil be as high as possible, and that cathode layer 175 be as thin as possible. For example, it is contemplated that individual cathode layers 175 have a specific capacitance of about 100–1,000 microfarads/cm$^2$. Suitable cathode foils are commercially available on a widespread basis. In still other embodiments, the cathode foil comprises materials or metals in addition to aluminum, aluminum alloys and "pure" aluminum.

Separator layer sheets 180*a* and 180*b* and outer separator layers of the electrode stack assembly 225 (FIG. 8) assembled from a plurality of stacked capacitor layers 227 are most preferably made from a roll or sheet of separator material. Separator layers 180 are preferably cut slightly larger than anode layers 170 and cathode layers 175 to accommodate misalignment during the stacking of layers, to prevent subsequent shorting between anode and cathode layers, and to otherwise ensure that a physical barrier is disposed between the anodes and the cathodes of the finished capacitor.

In one preferred embodiment of the capacitor layer 227 as depicted in FIG. 4, two individual separator layer sheets 180a and 180b form the separator layer 180 that is disposed between each anode layer 170 and cathode layer 175. Further single separator layer sheets 180a and 180b are disposed against the outer surfaces of the anode sheet 185c and the cathode layer 175d. When the sub-assemblies are stacked, the outermost single separator layer sheets 180a and 180b bear against adjacent outermost single separator layer sheets 180b and 180a, respectively, of adjacent capacitor layers so that two sheet separator layers 180 separate all adjacent cathode and anode layers of an electrode stack assembly 225.

It is preferred that separator layer sheets 180a and 180b and exterior separator layers between the electrode stack assembly and the case and cover be made of a material that: (a) is chemically inert; (b) is chemically compatible with the selected electrolyte; (c) may be impregnated with the electrolyte to produce a low resistance path between adjoining anode and cathode layers, and (d) physically separates adjoining anode and cathode layers. In one preferred embodiment, separator material is a pure cellulose, very low halide or chloride content Kraft paper having a thickness of about 0.0005 inches, a density of about 1.06 grams/cm$^3$, a dielectric strength of 1,400 Volts AC per 0.001 inches thickness, and a low number of conducting paths (about 0.4/ft$^2$ or less). Separator layer sheets 180a and 180b and outer separator layers 165a and 165b may also be made of materials other than Kraft paper, such as Manila paper, porous polymeric materials or fabric gauze materials. In such capacitor stacks assembled from a plurality of capacitor layers, a liquid electrolyte saturates or wets separator layers 180 and is disposed within the capacitor interior case chamber.

It will be understood by those skilled in the art that the precise number of capacitor layers 227 selected for use in a electrode stack assembly 225 will depend upon the energy density, volume, voltage, current, energy output and other requirements placed upon capacitor 265. Similarly, it will be understood by those skilled in the art that the precise number of notched anode sheets 190 and un-notched anode sheets 185, anode tabs 195, anode layers 170, cathode layers 175 and separator layers 180 selected for use in a given embodiment of capacitor layer 227 will depend upon the energy density, volume, voltage, current, energy output and other requirements placed upon capacitor 265. It will now become apparent that a virtually unlimited number of combinations and permutations respecting the number of capacitor layers 227, and the number of notched anode sheets 190 and un-notched anode sheets 185 forming anode layer 170, anode layers 170, anode tabs 195, cathode layers 175 and separator layers 180 disposed within each capacitor layer 227, may be selected according to the particular requirements of capacitor 265.

Figure 5:
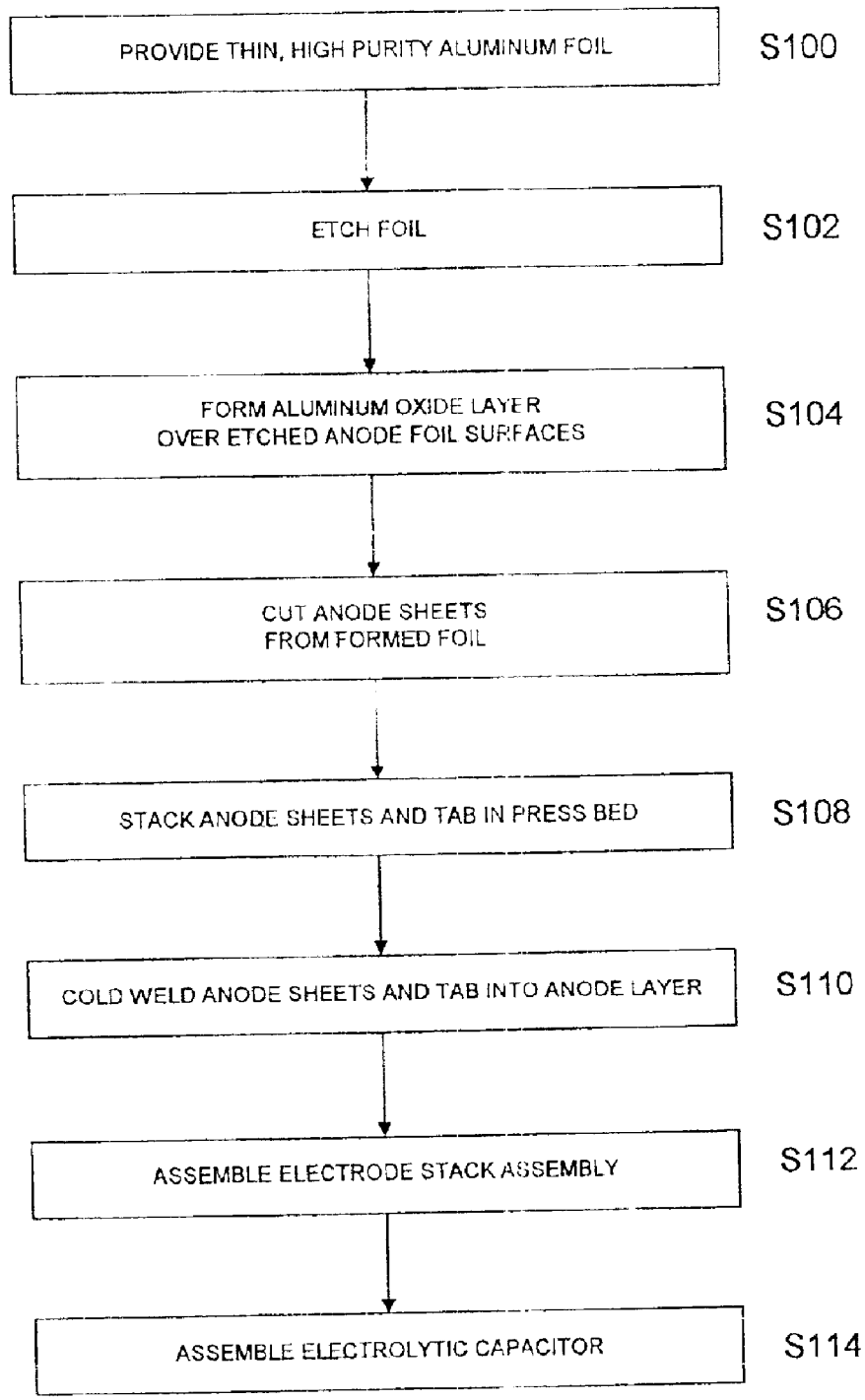
FIG. 5 is a flow chart illustrating the steps of forming an electrolytic capacitor in accordance with the invention.

FIG. 5 depicts the method of forming anode sheets, attaching the anode sheets together to form an anode layer and then fabricating an electrolytic capacitor using the anode layers. First, a thin aluminum foil of the type described above is provided in step S100, etched in step S102, "formed" in step S104, and cut into anode sheets 185/190 shown in FIG. 4 in step S106. The anodized, aluminum oxide, dielectric layers are grown in step S104 over the pores and the tunnels created in the etching step S102 in a manner known in the art.

The anode sheets 185/190 have opposed major anode sheet surfaces that can be highly etched in step S102 to form certain pores extending part way through the thickness of anode sheet to a sheet core layer and certain through-etched tunnels extending all the way through the sheet core layer to provide electrolyte wetting through the outer anode sheets to inner anode sheets of an anode layer. The large pores, small pores, large cross-section tunnels, and small cross-section tunnels provide enhanced surface area in comparison to the planar sheet surfaces prior to etching. However, some surface area potential is lost by virtue of overly large pores and tunnels. Conversely, ESR is increased by small tunnels that impede electrolyte and ion passage therethrough. Preferably, the etched anode foil has a high specific capacitance (at least about 0.3, at least about 0.5 or most preferably at least about 0.8 microfarads/cm$^2$), has a dielectric withstand parameter of at least 425 Volts DC, a thickness ranging between about 50 and about 200 micrometers, and a cleanliness of about 1.0 mg/m$^2$ respecting projected area maximum chloride contamination. The anode foil preferably has a rated surge voltage of 390 Volts, an initial purity of about 99.99% aluminum, a final thickness of about 104 micrometers, plus or minus about five micrometers, and a specific capacitance of about 0.8 microfarads per square centimeter. Suitable anode foils etched to specification are commercially available on a widespread basis.

The anode and cathode sheets are most preferably cut to shape in step S106 using dies having low wall-to-wall clearance, where inter-wall spacing between the substantially vertically-oriented corresponding walls of the punch and die is most preferably on the order of about 6 millionths of an inch per side. Larger or smaller inter-wall spacings between the substantially vertically-oriented corresponding walls of the punch and cavity, such as about 2–12 millionths of an inch may also be employed but are less preferred. The anode tab 195d is preferably cut from aluminum foil, and separator layers 180a, 180b are preferably cut from Kraft paper, respectively, in the same manner.

Such low clearance results in smooth, burr free edges along the peripheries of anode sheets 185 and 190 and anode tabs 195 as well as cathode layers 175, cathode tabs 176 and the separator layers 180a, 180b of each capacitor layer 170. Smooth, burr free edges on the walls of the dies have been discovered to be critical respecting reliable performance of a capacitor. The presence of burrs along the peripheries of anode sheets 185 and 190, anode and cathode tabs 195, 176, cathode layers 175 and separator layers 180 may result in short circuit and failure of the capacitor. The means by which anode foil, cathode foil, and separator materials are cut may have a significant impact on the lack or presence of burrs and other cutting debris disposed about the peripheries of the cut members. The use of low clearance dies produces an edge superior to the edge produced by other cutting methods, such as steel rule dies. The shape, flexibility and speed of a low clearance die have been discovered to be superior to those achieved by laser or blade cutting. Other methods of cutting or forming anode sheets 185 and 190, anode tabs 195, cathode layers 175 and separator layers 180 include, but are not limited to, steel rule die cutting, laser cutting, water jet cutting and blade cutting. Further details relating to preferred methods of cutting the anode foil to form anode sheets and sandwiching anode sheets together to form an anode layer 170 are set forth in the above-referenced, commonly assigned, '133 patent. The anode sheets 185/190 and anode tab 195d are assembled together in step S110 to form anode layers 170, e.g. anode layer 170d of FIG. 4, in accordance with the following description of the cold welding process in reference to FIGS. 7–10.

Figure 6:
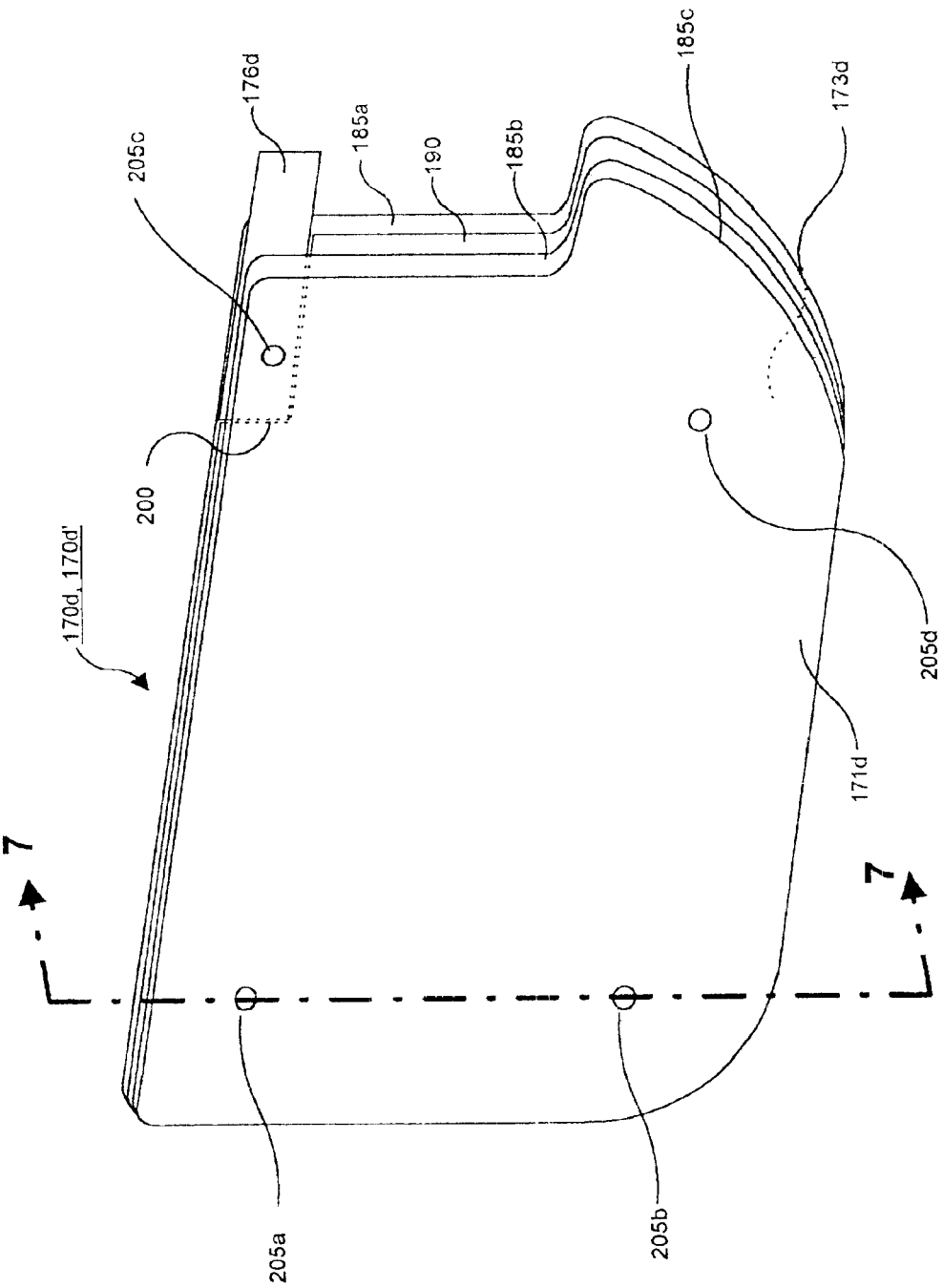
FIG. 6 is a perspective view of the anode layer assembled from anode sheets employing precision cold welding in accordance with the preferred embodiments of the invention.
Figure 7:
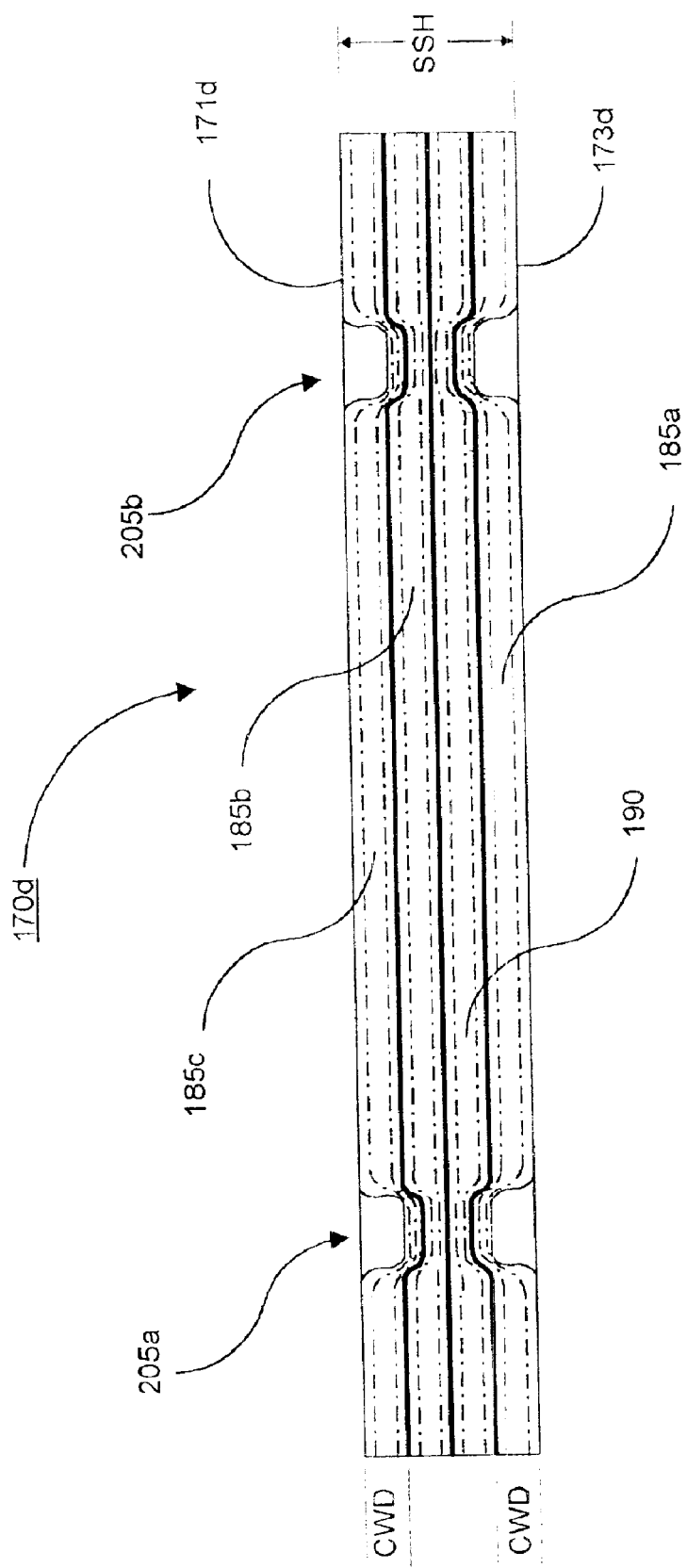
FIG. 7 is a side cross-section view taken along line 7—7 of FIG. 6 showing the anode sheets cold welded together in accordance with the preferred embodiments of the present invention.

In accordance with the present invention, the side-by-side stacked multiple anode sheets 185/190 and the anode tab 195d are assembled into an anode sheet stack 170d' in the alignment shown in FIG. 6 in a press bed in step S110 and precision cold welded together in step S112 to form the anode layer 170d. As shown in FIGS. 6 and 7, a plurality of cold welds 205a–205d are made in step S112 extending inward from the stack sides 171d and 173d of the stack of anode sheets that form the anode layer 170d to a CWD. The cold welds 205a, 205b, and 205d mechanically and electrically connect the aluminum valve metal of the core layer of each sheet 185/190 together. The anode tab of anode sheet 190 is thereby coupled electrically via cold weld 205c with the core layers of the anode sheets 185a14 185c. The cold welds 205a–205d can be circular in cross-section as depicted in FIGS. 6 and 7 or any convenient shape, depending upon the shape of the weld pin described further below.

The cold weld deformation of the anode sheets 185/190 is effected by simultaneously driving four sets of first and second axially aligned cold weld pins into respective first and second stack sides of the stacked anode sheets 185/190 to substantially equal weld depths CWD as shown in FIG. 7. In this way, uniformly sized and strong cold welds 205a–205d of all of the anode sheets are achieved while minimizing damage to adjoining oxide layers of the anode sheets 185/190 so that capacitance per unit area is maximized. In particular, the sheet stack height SSH shown in FIG. 7 is not appreciably compressed in all but the areas of the cold welds 205a–205d in the cold welding process. It will be understood that more of fewer than four cold welds 205 can be formed in accordance with the present invention.

Figure 8:
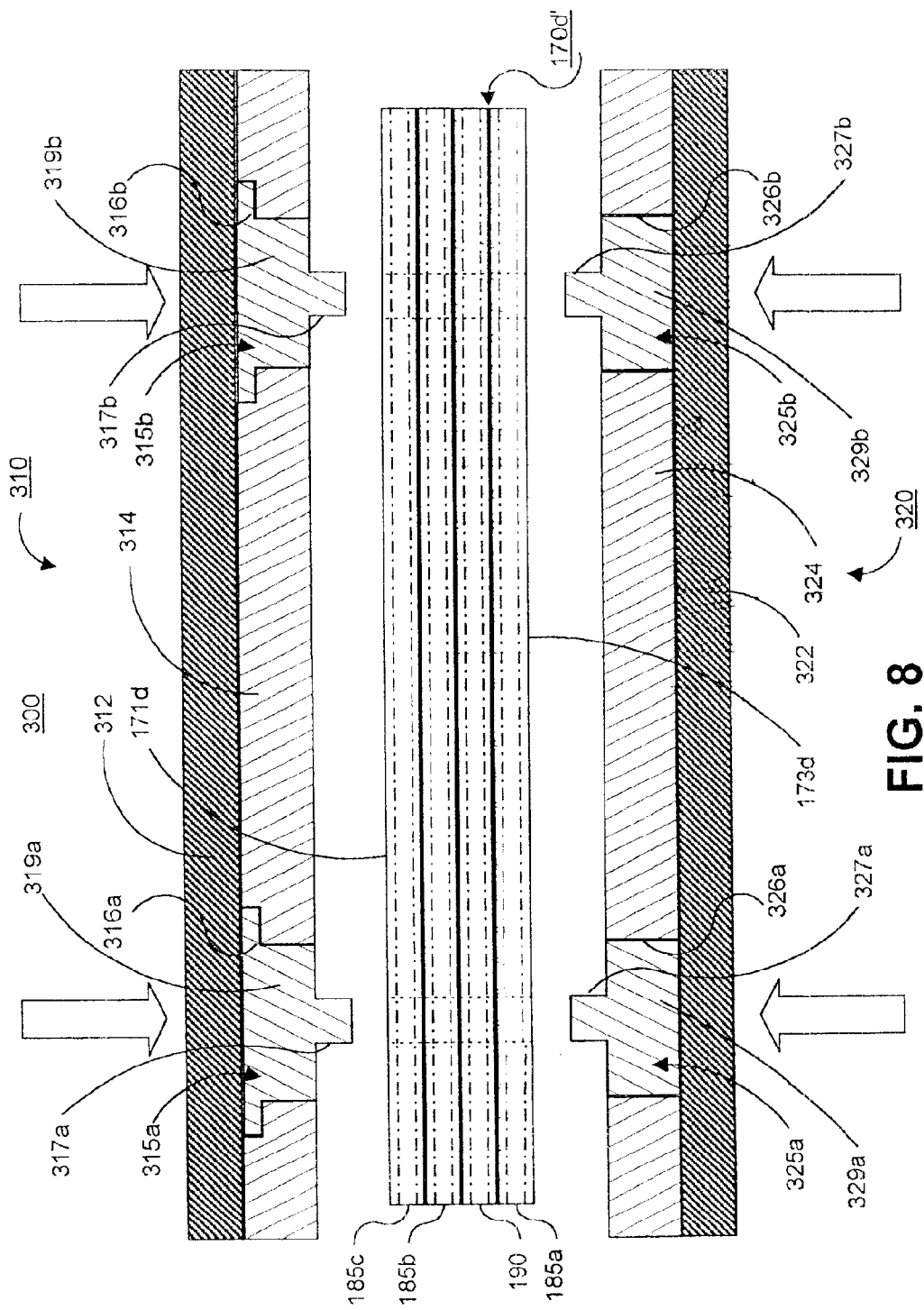
FIG. 8 is a side cross-section view of the stack of anode sheets positioned in relation to one embodiment of a cold weld press fixture of the present invention for forming the cold welds of the anode sheets illustrated in FIGS. 6 and 7.

The cold welding is effected through the use of a vertical press of the type shown in FIG. 5(b) of the above-referenced commonly assigned, '133 patent or any other suitable horizontal or vertical press employing the press fixture 300 of FIG. 8. The press fixture 300 comprises a first or upper plate assembly 310 and a second or lower plate assembly 320 arranged to receive the anode sheet stack 170d' supported between the first and second plate assemblies 310 and 320. The press fixture 300 or the first and second plate assemblies 310 and 320 preferably include registration pins or a registration frame (not shown) for maintaining the anode sheets 185/190 aligned in the anode sheet stack 170d'. The first and second plate assemblies 310 and 320 each support one or preferably a plurality of cold weld dies; for example, the first and second plate assemblies 310 and 320 each support four cold weld dies arranged in a planar array to form the four cold welds 205a, 205b, 205c, 205d of FIG. 6. The press fixture 300 preferably further includes an alignment and guide mechanism extending between the first and second plate assemblies 210 and 320 to maintain the first and second plate assemblies 210 and 320 substantially parallel to one another and in registration with one another as they are moved toward and away from one another in any of the ways well known in the art.

The first and second plate assemblies 310 and 320 of press fixture 300 shown in FIG. 8 each comprise respective first and second substantially planar force plates 312 and 322 and respective first and second substantially planar die holders 314 and 324. The first and second die holders 314 and 324 each have four die receptacles, and four cold weld dies held within four receptacles. The first plate assembly 310, second plate assembly 320, and interposed anode sheet stack 170d' are depicted in cross-section in FIG. 8, wherein the die receptacles 316a and 316b of die holder 314 hold dies 315a and 315b, respectively, and the die receptacles 326a and 326b of die holder 324 hold dies 315a and 325b, respectively, for forming the cold welds 205a and 205b shown in FIGS. 6 and 7.

In the preferred embodiment illustrated in FIG. 8, the cold weld dies 315a and 315b are fabricated with cold weld pins 317a and 317b extending from die bodies 319a and 319b respectively. Similarly, the cold weld dies 325a and 325b are fabricated with cold weld pins 327a and 327b extending from die bodies 329a and 329b respectively. The die bodies 319a and 319b fit or plug into die body receptacles 316a and 316b of the first substantially planar die holder 314, and die bodies 329a and 329b, respectively, fit or plug into die body receptacles 326a and 326b, of the second substantially planar die holder 324.

The cold weld pins 317a and 317b extend outward from the first die holder 314 toward the first stack side 171d of the anode sheet stack 170d', and the cold weld pins 327a and 327b extend outward from the second die holder 324 toward the first stack side 173d of the anode sheet stack 170d'. In this way, the cold weld pins 317a and 327a are maintained in substantially axial alignment through the anode sheet stack 170d' in the area where cold weld 205a is to be made, and the cold weld pins 317b and 327b are maintained in substantially axial alignment through the anode sheet stack 170d' in the area where cold weld 205b is to be made. It will be understood that the first and second die holders 314 and 324 contain two further receptacles that hold two more cold weld dies to form the cold welds 205c and 205d of FIG. 6.

All of the cold weld pins 317a, 317b and 327a, 327b have substantially equal pin lengths extending away from their respective die bodies 319a, 319b and 329a, 329b and the substantially planar inward surfaces of the respective die holders 314 and 324. The first force plate 312 bears against all of the of the first cold weld die bodies 319a, 319b and the first die holder 314, and the second force plate 322 bears against all of the of the second cold weld die bodies 329a, 329b and the first die holder 324. The force of the press is applied equally to all of the first and second cold weld dies through the respective first and second force plates 312 and 322.

In this exemplary embodiment, it is assumed that the press fixture 300 is to be mounted into a vertical press. In a vertical press, the first and second plate assemblies 310 and 320 are referred to as upper and lower plate assemblies, respectively, situated above the first or upper stack side 171d and the second or lower stack side 173d, respectively, of the horizontally stacked anode sheet stack 170d. The lower plate assembly 320 is preferably supported in a press bed, whereby the lower stack side 173d of the anode sheet stack rests upon the lower cold weld pins 325a, 325b, etc., and are maintained in registration. The upper plate assembly 310 can be suspended on a movable press arm that is brought down against the upper stack side 171d of the anode sheet stack 170d until the prescribed CWD is achieved by each cold weld pin 317a, 317b, 327a, 327b, etc. Therefore, the die bodies 319a and 319b of the upper cold weld dies 315a and 315b and the upper die receptacles 316a and 316b are shaped or keyed to hold the upper cold weld dies 315a and 315b in place when the upper plate assembly 310 is suspended above upper side 171d. The upper dies could be retained in the upper die receptacles by other known interlocking or friction mechanisms, e.g., springs, pipe threads, keys or the like.

Figure 9A:
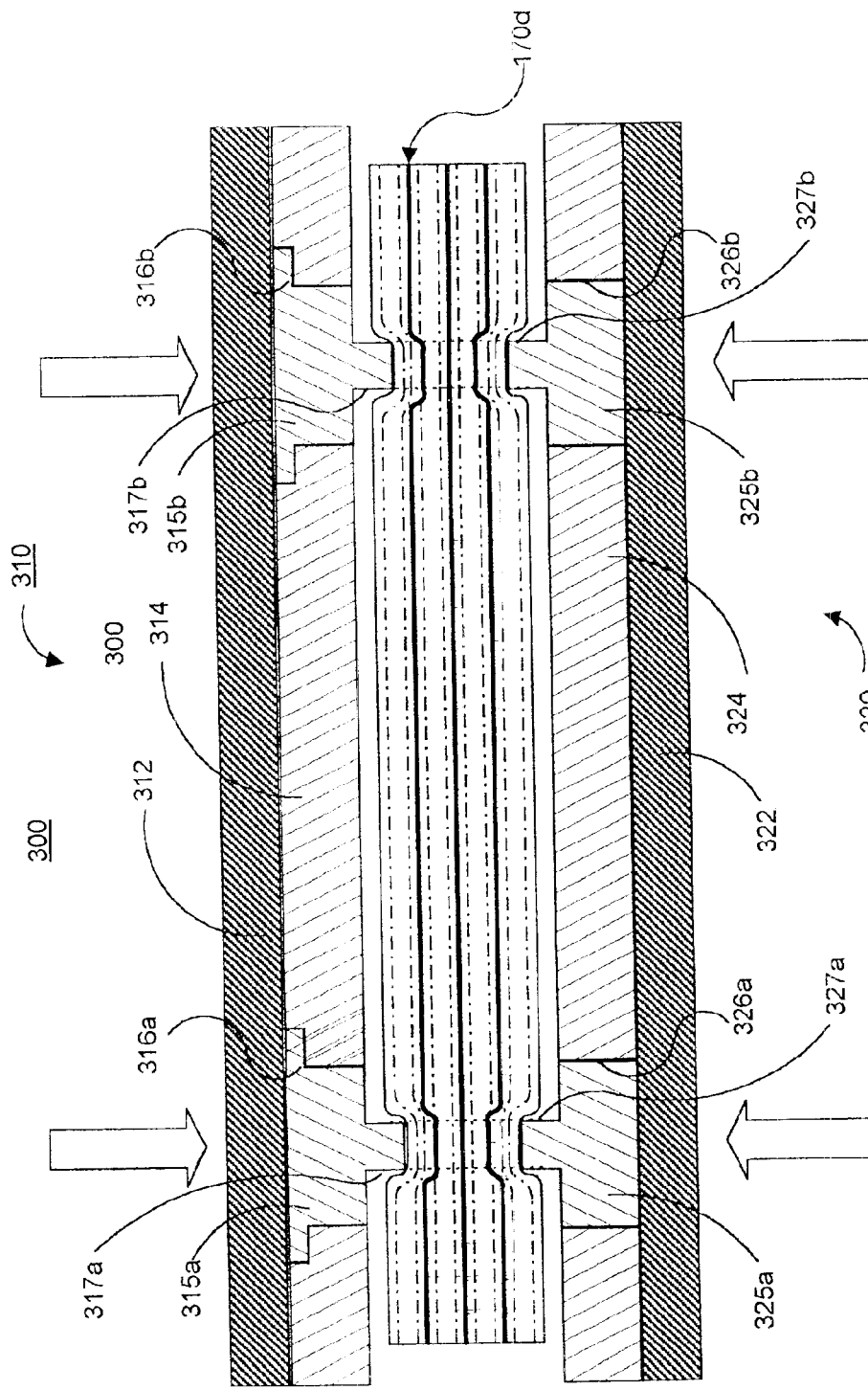
FIGS. 9($a$) and 9($b$) are side cross-section views showing the steps of cold welding the anode sheets together employing the cold weld press fixture of FIG. 8 in accordance with a first embodiment of the invention to electrically and mechanically join the valve metals of the anode layers.
Figure 9B:
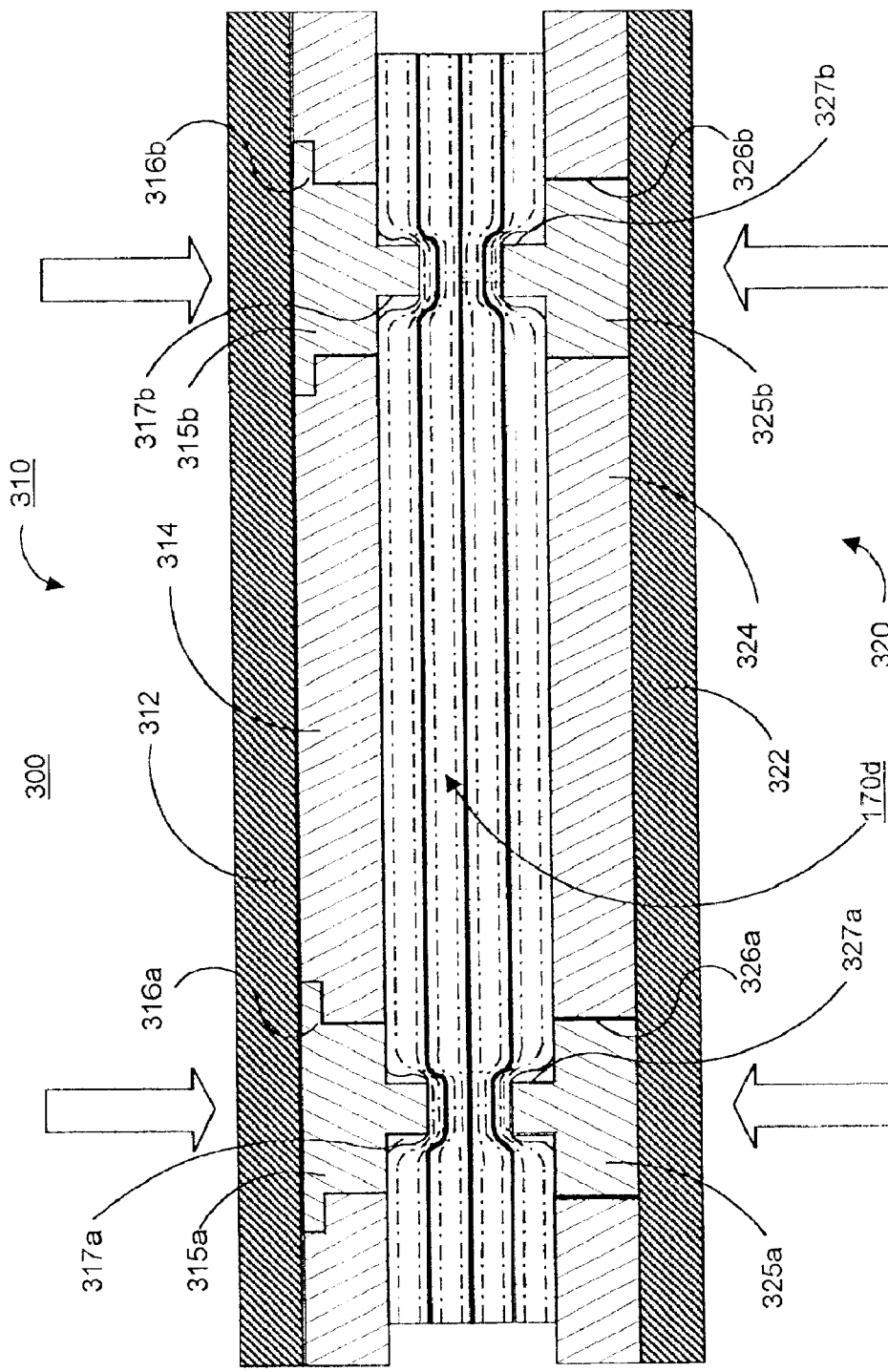

The cold welding process is further depicted in FIGS. 9(a) and 9(b). In FIG. 9(a), the press force is applied against the first or upper and second or lower force plates 312 and 314. The force plates 312 and 314 distribute the press force across outermost surfaces of the first or upper die holder 314 and second or lower die holder 324 and to the cold weld pins 317a, 317b, 327a, 327b etc supported thereby. In FIG. 9(a), the cold weld pins 317a, 317b, 327a, 327b are depicted partially crushing the anode sheets 185/190 together in the areas of the cold welds 205a and 205b. In FIG. 9(b), the cold weld pins 317a, 317b, 327a, 327b are depicted fully extended into the anode sheets 185/190 in the areas of the cold welds 205a and 205b. The cold welds 205a and 205b have a CWD substantially equal to the die pin lengths when the stack sides 171d and 173d are contacted by the substantially planar first or upper and second or lower die holders 314 and 324. The cold welds 205a, 205b, 205c, 205d of FIG. 6 are thereby made having the CWD relative to the SSH depicted in FIG. 8.

The CWD can also be regulated by feedback of measured applied force such that the advancement of the first and second plate assemblies is halted when a predetermined applied force is measured. Or the CWD can be regulated by presetting the press limit advancement of the first and second plate assemblies to a fixed distance.

The cold weld pins 317a, 317b, 327a, 327b, etc. have a relatively small pin cross section area relative to the area of the first and second stack sides 171d and 173d of the anode sheet stack 170d. Therefore, the force required to press the cold weld pins 317a, 317b, 327a, 327b, etc into the anode sheet stack 170d from the first and second stack sides 171d and 173d in substantially axially alignment is considerably less than the force required to compress the anode sheet stack 170d' as a whole. Therefore, if the applied force is limited, the anode sheet stack 170d' can itself constitute a CWD stop that is operative when the substantially planar surfaces of the substantially planar die holders 312, 314 contact the first and second outermost surfaces 171d and 173d. In this way, the final separation apart of the first and second plate assemblies is substantially equal to the SSH.

Figure 10A:
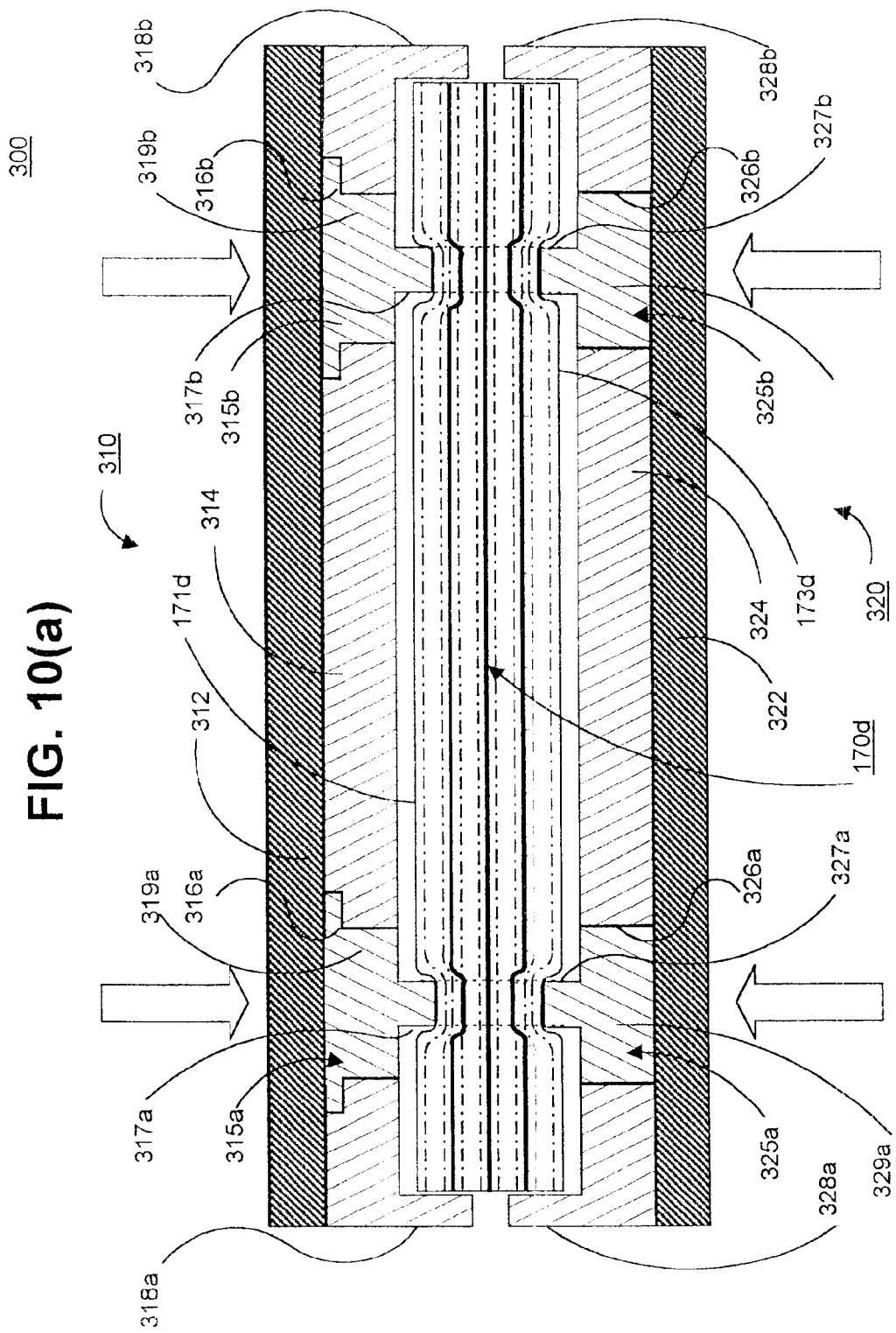
FIGS. 10($a$) and 10($b$) are side cross-section showing the steps of cold welding the anode sheets together employing the cold weld press fixture of FIG. 8 modified to have built-in stop members that limit and equalize the cold weld depths in the anode layers and/or registration members that register the anode sheets of the anode sheet stack during cold welding.
Figure 10B:
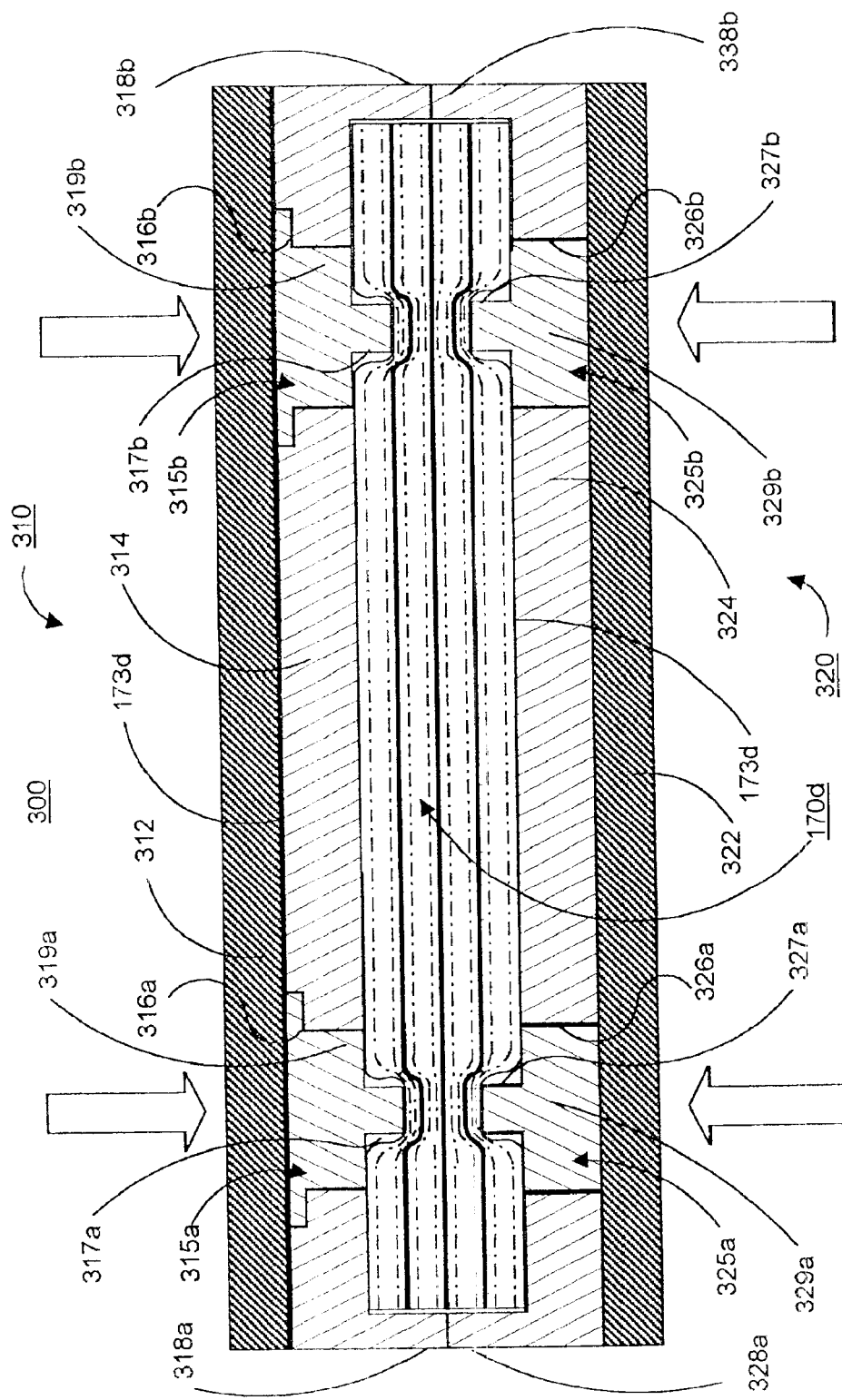

Alternatively or additionally, the final separation apart of the first and second plate assemblies can be made substantially equal to the SSH when the first and second plate assemblies 310 and 320 contact one another. In one way of accomplishing this, the press fixture or the first and second plate assemblies 310 and 320 optionally include CWD stop members that limit the CWD achieved by each cold weld pin 317a, 317b, 327a, 327b. In the embodiments depicted in FIGS. 9(a) and 9(b), the die holder 314 is modified to have peripherally disposed stop members 318a and 318b, and the die holder 324 is modified to have peripherally disposed stop members 328a and 328b. The stop members 318a, 318b, 328a, 328b can be pins or a continuous rim. The stop lengths are correlated to the SSH and the desired CDW that is achieved in FIG. 10(b) when the first or upper stop members 318a and 318b contact the second or lower stop members 328a, 328b. Generally, the stop lengths would ensure that the distance between the facing surfaces of the first or upper die holder 314 and the second or lower die holder 324 would be substantially equal to or greater than the SSH when the first or upper stop members 318a and 318b contact the second or lower stop members 328a, 328b. While equal stop lengths are depicted in FIGS. 10(a) and 10(b), it will be understood that the first or upper stop members 318a and 318b can be longer or shorter than the second or lower stop members 328a, 328b as long as they contact one another prior to or when the facing surfaces of the first or upper die holder 314 and the second or lower die holder 324 contact the first and second stack sides 171d and 173d, respectively. In this regard, it will also be understood that the second or lower stop members 328a, 328b can be arranged in height and spacing to register the anode sheets of the anode sheet stack 170d'.

The method of the invention is preferably also employed in these same ways to cold weld the anode tab 195d to the anode sheets 185a, 185b, 185c by the cold weld 205c depicted in FIG. 6.

Other variations of the preferred embodiments may also be implemented. The pluralities of first and second cold weld dies can be fabricated integrally with the respective first and second force plate such that the cold weld die bodies are integrally subsumed into the cold weld plates and the cold weld pins extend from the force plates by a cold weld pin length that is correlated to the CWD. Preferably, however, the single ones or pluralities of first and cold weld dies are separate from the first and second force plates so that the single ones or pluralities of first and cold weld dies can be replaced as the cold weld pins wear out through use.

Alternatively, the first and second substantially planar force plates 312 and 322 and respective first and second substantially planar die holders 314 and 324 can be combined into unitary support and force distributing plates provided with the receptacles for receiving the cold weld die bodies. The combined force plates 312 and 322 and respective first and second substantially planar die holders 314 and 324 support the cold weld pins extending from the substantially planar body surface by a cold weld pin length that is correlated to the CWD.

In another variation on any of the above embodiments, the cold weld die bodies of a plurality of first and second cold weld dies can be joined together as first and second unitary cold weld dies having unitary cold weld die bodies shaped to be received in a conformal receptacle. The unitary cold weld die bodies are substantially planar and integrally support the cold weld pins extending from the substantially planar body surface by a cold weld pin length that is correlated to the CWD.

The particular shape, number and manner of fabrication and formation of the anode sheets of the anode layer 170d described herein is merely illustrative, and does not limit the scope of the present invention in any way. Among other things, the present invention can be employed to electrically and mechanically connect the valve metal cores of any number of stacked, etched and anodised, anode sheets and any configurations of the anode sheets.

Figure 12:
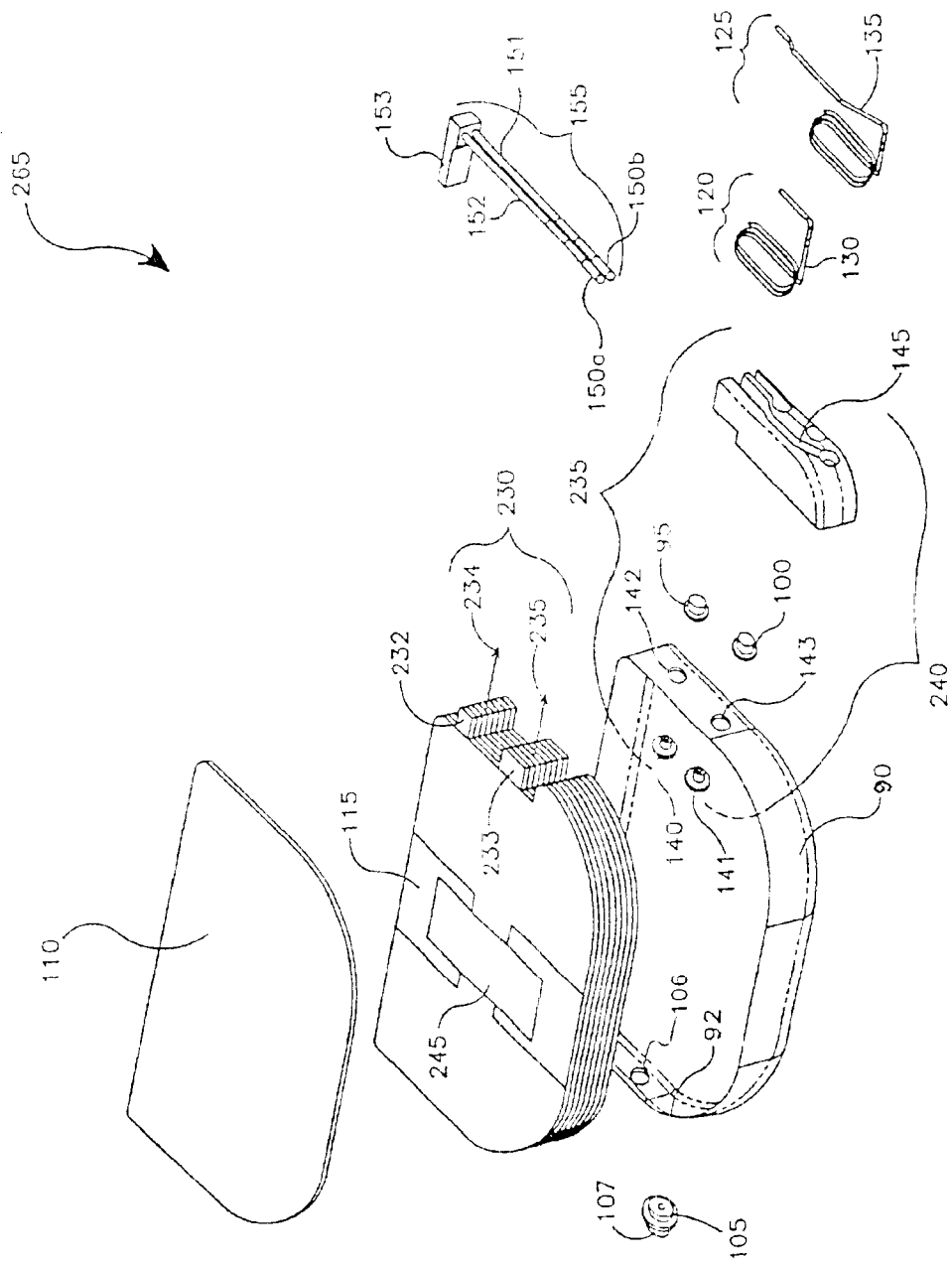
FIG. 12 is an exploded top perspective view of the electrode stack assembly ready to be fitted together with the remaining components of the embodiment of an electrolytic capacitor.

FIGS. 11 and 12 illustrate the formation of the electrode stack assembly 225 in accordance with step S114 of FIG. 5 in relation to the capacitor case cover 110, the case housing 90 and other components of the capacitor 265 illustrated in FIG. 8. The electrode stack assembly 225 comprises a plurality of capacitor layers 227a–227h assembled as described above with reference to FIG. 4 and having anode tabs 195a–195h and cathode tabs 176a–176h. The voltage developed across each capacitor layer disposed within electrode stack assembly 225 most preferably ranges between about 360 and about 390 Volts DC. As described below, the various anode sub-assemblies of electrode stack assembly 225 are typically connected in parallel electrically, as are the various cathode layers of electrode stack assembly 225. The electrode stack assembly 225 is merely illustrative, and does not limit the scope of the present invention in any way respecting the number or combination of anode layers 170, cathode layers 175, separator layers 180, anode tabs 195, cathode tabs 176, and so on. The number of electrode components is instead determined according to the total capacitance required, the total area of each layer, the specific capacitance of the foil employed and other factors.

The capacitor layers 227a 227h are stacked together between outer paper layers 165a and 165b, and outer wrap 115 is folded over the top of electrode stack assembly 225 in step S112. Wrapping tape 245 is then holds outer wrap 115 in place and secures the various components of electrode stack assembly 225 together. Outer wrap 115 is most preferably die cut from separator material described above or other suitable materials such as polymeric materials, suitable heat shrink materials, suitable rubberized materials and synthetic equivalents or derivatives thereof, and the like. Wrapping tape 245 is most preferably cut from a polypropylene-backed acrylic adhesive tape, but may also be replaced by a staple, an ultrasonic paper joint or weld, suitable adhesives other than acrylic adhesive, suitable tape other than polypropylene-backed tape, a hook and corresponding clasp and so on. Usable alternatives to outer wrap 115 and wrapping tape 245 and various stacking and registration processes by which electrode stack assembly 225 is most preferably made are not material to the present invention and are disclosed in the above-referenced, commonly assigned, '133 patent.

FIG. 12 shows an exploded top perspective view of one embodiment of an exemplary, case neutral, electrolytic capacitor 265 employing the electrode stack assembly 225 therein and the electrical connections made to the gathered anode and cathode tabs 232 and 233. This embodiment includes anode feedthrough 120 and cathode feedthrough 125 most preferably having coiled basal portions 121 and 126, respectively. Feedthroughs 120 and 125 provide electrical feedthrough terminals for capacitor 265 and gather gathered anode tabs 232 and gathered cathode tabs 233 within basal portions 121 and 126 for electrical and mechanical interconnection.

Feedthrough wire is first provided and trimmed to length for construction of feedthroughs 120 and 125. One end of the trimmed wire is coiled such that its inside diameter or dimension is slightly larger than the diameter or dimension required to encircle gathered anode tabs 232 or gathered cathode tabs 233. Gathered anode tabs 232 are next gathered, or brought together in a bundle by crimping, and inside diameter 131 of anode feedthrough coil assembly 120 is placed over gathered anode tabs 232 such that anode feedthrough pin 130 extends outwardly away from the base of gathered anode tabs 232. Similarly, gathered cathode tabs 233 are gathered and inside diameter 136 of cathode feedthrough coil assembly 125 is placed over gathered cathode tabs 233 such that cathode feedthrough pin 135 extends outwardly away from the base of cathode tab 233. Coiled basal portions 121 and 126 of anode and cathode feedthroughs 120 and 125 are then most preferably crimped onto anode and cathode tabs 232 and 233, followed by trimming the distal ends thereof, most preferably such that the crimps are oriented substantially perpendicular to imaginary axes 234 and 235 of gathered anode and cathode tabs 232 and 233. Trimming the distal ends may also, but less preferably, be accomplished at other non-perpendicular angles respecting imaginary axes 234 and 235.

In some preferred methods, a crimping force is applied to feedthrough coils 121 and 126 and tabs 232 and 233 throughout a subsequent preferred welding step. In one method, it is preferred that the crimped anode and cathode feedthroughs be laser or ultrasonically welded along the top portion of the trimmed edge of the distal ends to anode and cathode tabs 232 and 233. Following welding of feedthroughs 120 and 125 to gathered anode tabs 232 and gathered cathode tabs 233, respectively, pins 130 and 135 are bent for insertion through feedthrough holes 142 and 143 of case 90.

Many different embodiments of the feedthroughs and means for connecting the feedthrough pins to anode and cathode tabs exist other than those shown explicitly in the figures and are described in the above-referenced, commonly assigned, '133 patent.

A case sub-assembly is also created from case 90, anode ferrule 95, cathode ferrule 100, and fill port ferrule 105 are first provided. In a preferred embodiment of capacitor 265, the case 90 and cover 110 are fabricated of aluminum. In other embodiments, case 90 or cover 110 may be fabricated of any other suitable corrosion-resistant metal such as titanium or stainless steel, or may alternatively be fabricated of a suitable plastic, polymeric material or ceramic. The anode ferrule 95 and cathode ferrule 100 are welded to the aluminum case side wall to fit around anode and cathode feedthrough ferrule holes 142 and 143, and a fill port ferrule is welded to the case side wall around a fill port hole 106. The welding steps form no part of the present invention and various ways of doing so are disclosed in detail in the above-referenced, commonly assigned, '133 patent.

Wire guides 140 and 141 fit within center holes of ferrules 95 and 100 respectively and receive, center, and electrically insulate anode and cathode pins 130 and 135 from the case 90, anode ferrule 95, and cathode ferrule 100. The formation and assembly of the wire guides 140, 141 with the ferrules 95, 100 and cathode pins 130, 135 form no part of the present invention and examples thereof are disclosed in detail in the above-referenced, commonly assigned, '133 patent. Similarly, the insertion of the cathode pins 130, 135 through the wire guides 140, 141 and the seating of the electrode stack assembly 225 coupled thereto into the interior case chamber of case 90 form no part of the present invention and examples thereof are disclosed in detail in the above-referenced, commonly assigned, '133 patent.

A connector assembly is also coupled with the exposed, outwardly extending pins 130 and 135. In one preferred embodiment, connector block 145 is disposed atop or otherwise connected to case 90 and/or cover 110, and has wire harness 155 attached thereto and potting adhesive disposed therein. However, the particular configuration of connector block 145 and its method of fabrication do not play a role in the practice of the present invention. Examples thereof are disclosed in detail in the above-referenced, commonly assigned, '133 patent.

Figure 13:
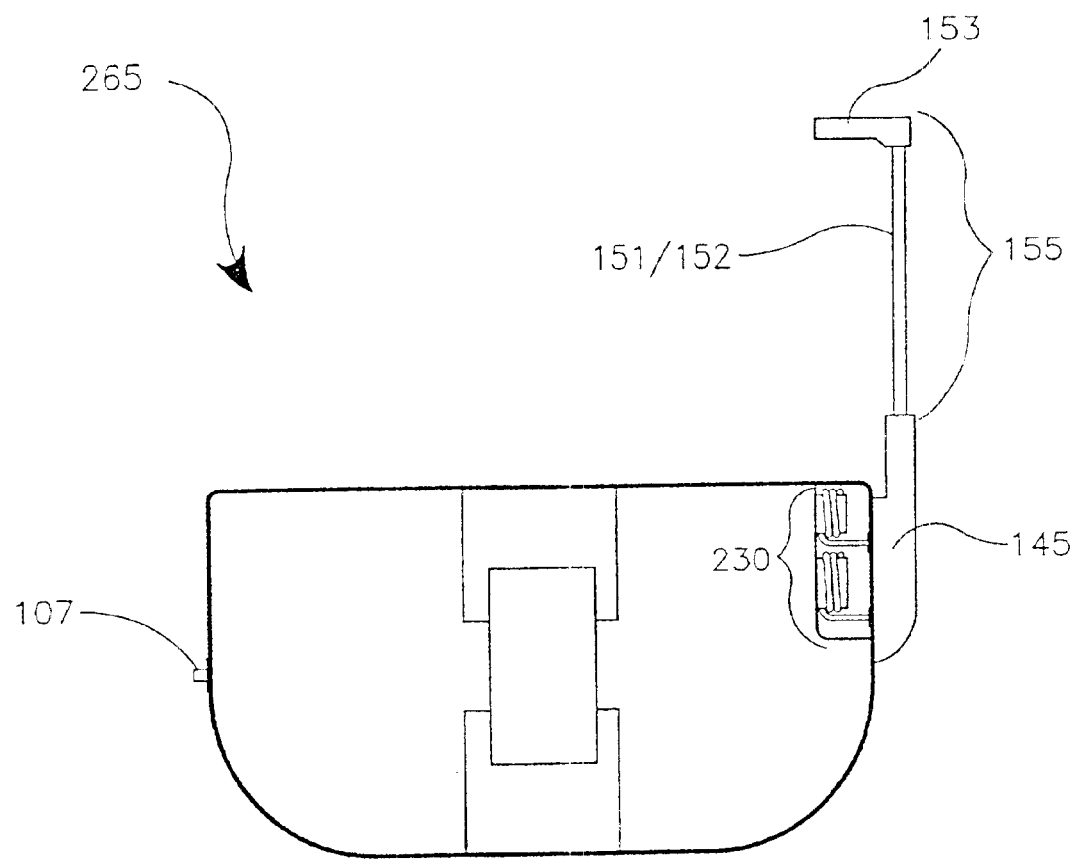
FIG. 13 is a plan view of the electrode stack assembly fitted into the capacitor housing together and attached to the remaining components of the embodiment of an electrolytic capacitor prior to attaching the cover to the housing and filling the capacitor with electrolyte.

In the illustrated embodiment, pre-formed plastic connector block 145 is placed on anode ferrule 95 and cathode ferrule 100 by guiding anode feedthrough pin 130 through connector block anode feedthrough hole 300, and then guiding cathode feedthrough pin 135 through connector block cathode feedthrough hole 305. Connector block 145 is next seated flush against the exterior surface of case 90. Anode feedthrough pin 130 is then inserted into anode crimp tube 150b of wire harness 155. Cathode feedthrough pin 135 is then inserted into cathode crimp tube 150a of wire harness 155. Crimp tubes 150a and 150b are then crimped to feedthrough pins 130 and 135. The distal or basal portions of crimp tubes 150a and 150b are crimped on insulated anode lead 151 and insulated cathode lead 152, respectively. An epoxy adhesive is then injected into voids in the connector block 145 to insulate the crimped connections, seal the wire guides 140 and 141, case 90 and ferrules 95 and 100, and provide strain relief to feedthrough pins 130 and 135 and to the feedthrough wire crimp connections. Insulated leads 151 and 152 are likewise connected to terminal connector 153 that forms the female end of a slide contact and is adapted to be connected to electronics module 360 in FIG. 3(d). The completed assembly is depicted in FIG. 13.

Figure 14:
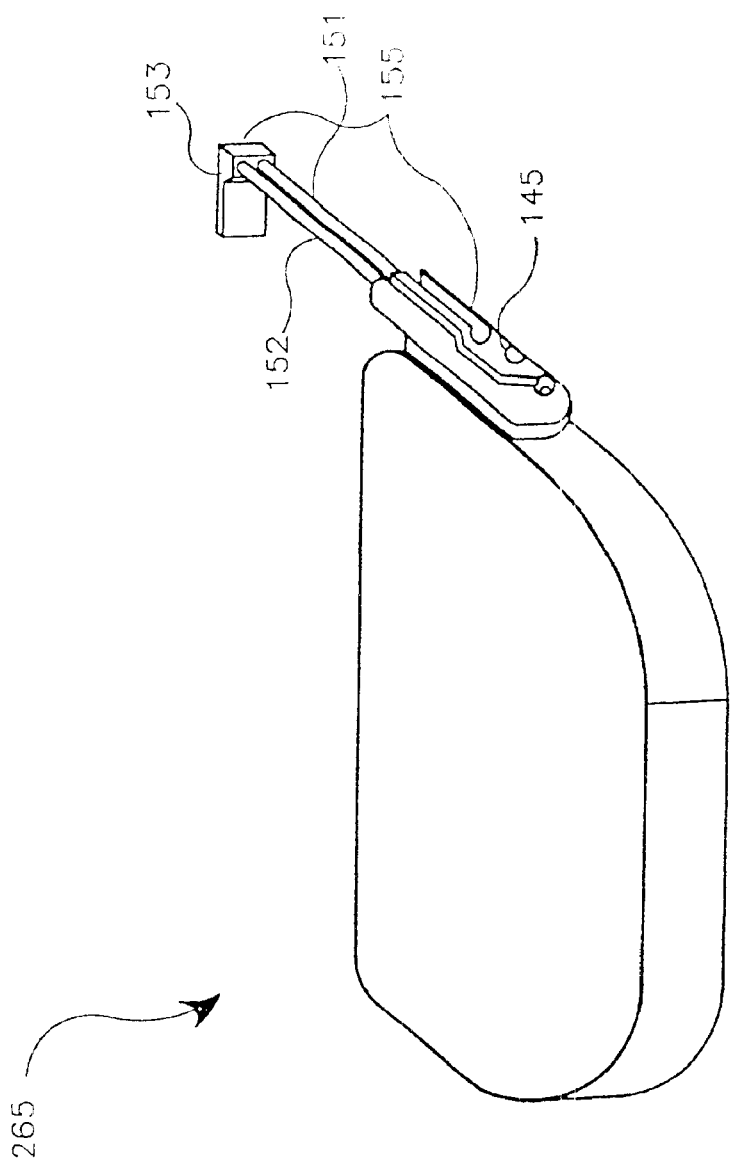
FIG. 14 is a plan view of the completed embodiment of an electrolytic capacitor in accordance with the invention.

The life of capacitor 265 may be appreciably shortened if solvent vapor or electrolyte fluid escapes from the interior of capacitor 265. Moreover, if capacitor 265 leaks electrolyte, the electrolyte may attack the circuits to which capacitor 265 is connected, or may even provide a conductive pathway between portions of that circuit. The cover 110 is placed upon the upper edge 92 of the case side wall, the upper edge 92 is crimped over the cover edge, and the joint therebetween is laser welded all in a manner disclosed in the above-referenced '133 patent, for example, that forms no part of the present invention. The resulting capacitor 265 depicted in FIG. 14 thus most preferably includes hermetic laser welded seams between joint case 90 and cover 110, and between ferrules 95,100, and 105 and case 90. Additionally, anode feedthrough portion 236 and cathode feedthrough portion 240 most preferably have an adhesive seal disposed therein for sealing the ferrule walls and the feedthrough wires.

The interior of capacitor 265 not occupied by the electrode stack assembly 225 is filled with electrolyte through the fill port 107 welded at fill port ferrule 105 into hole 106, aging cycles are conducted, and the fill port is then closed. The filling and aging are accomplished in a plurality of vacuum impregnation cycles and aging cycles form no part of the present invention and examples thereof are disclosed in detail in the above-referenced, commonly assigned, '133 patent. The electrolyte may be any suitable liquid electrolyte for high voltage electrolytic capacitors. In a preferred embodiment of the present invention, the electrolyte is an ethylene glycol based electrolyte having an adipic acid solute. It is contemplated that other liquid electrolytes suitable for use in high voltage capacitors may also be employed.

During capacitor charging, the ethylene glycol based electrolyte releases hydrogen gas that accumulates within the interior capacitor chamber and eventually can cause the base and cover to bulge outward. In accordance with a preferred embodiment of the present invention, hydrogen gas is released through the lumen of fill port 107 while loss of liquid or vaporized electrolyte is prevented.

It will be understood that the capacitor 265 may alternatively be fabricated as a case negative capacitor where case 90 and cover 110 are electrically connected to the cathode layers and are therefore at the same electrical potential as the cathode layers, i.e., at negative potential.

The preceding specific embodiments are illustrative of a capacitor structure and method of fabrication thereof and its incorporation into an IMD in accordance with the present invention. It is to be understood, therefore, that other expedients known to those skilled in the art or disclosed herein, and existing prior to the filing date of this application or coming into existence at a later time may be employed without departing from the invention or the scope of the appended claims.

All patents and printed publications disclosed herein are hereby incorporated by reference herein into the specification hereof, each in its respective entirety.

What is claimed is:

1. A method of fabricating an anode layer of an electrolytic capacitor from a plurality of anode sheets comprising:
   providing the plurality of anode sheets fabricated of a formed valve metal each having first and second sheet sides bounded by an anode sheet edge,
   stacking the plurality of anode sheets in side-by-side relation in an anode sheet stack having first and second stack sides and a stack height between the first and second stack sides
   positioning the anode stack in a press fixture comprising a first plate assembly facing the first stack side and a second plate assembly facing the second stack side, the first plate assembly further comprising a plurality of first cold weld dies each having a first cold weld pin extending from a first cold weld die body, the first weld dies mounted in a first planar array with respect to a first force plate for distributing force to the plurality of first cold weld die bodies and such that the first cold weld pins extend toward the first stack side, and the second plate assembly further comprising a plurality of second cold weld dies each having a cold weld pin extending from a cold weld die body, the second cold weld dies mounted in a second planar array with respect to a second force plate for distributing force to the plurality of second cold weld die bodies and such that the second cold weld pins extend toward the second stack side, first and second planar arrays dimensionally aligned to axially align each first cold weld pin of the first planar array with a respective second cold weld pin of the second planar array;
   advancing one or both of the first and second plate assemblies toward the first and second stack sides, respectively, to advance the first cold weld pins into the first stack side and the second cold weld pins into the second stack side; and
   stopping the advancement of the first and second cold weld pins into the first and second stack sides, respectively, when the first and second cold welds are advanced to substantially equal first and second cold weld depths into the respective first and second stack sides, whereby the valve metals of the anode sheets are cold welded together.

2. The method of claim 1, wherein:
   the first plate assembly comprises a first planar force plate and a substantially planar first die holder having a plurality of die body receptacles formed therein to removably receive the plurality of first cold weld die bodies and fix the first cold weld pins in the first planar array with the first cold weld pins extending substantially equal first pin lengths from the first die holder; and
   the second plate assembly comprises a second planar force plate and a substantially planar second die holder having a plurality of die body receptacles formed therein to removably receive the plurality of second cold weld die bodies and fix the second cold weld pins in the second planar array with the second cold weld pins extending substantially equal second pin lengths from the second die holder.

3. The method of claim 2, wherein:
   the die body receptacles of the first die holder extends through the first die holder, and the first force plate bears against and applies force to the first die bodies located in the first die body receptacles; and
   the die body receptacles of the second die holder extends through the second die holder, and the first force plate bears against and applies force to the second die bodies located in the second die body receptacles.

4. The method of claim 3, wherein the first die holder and the first force plate are separable from one another, and the second die holder and the second force plate are separable from one another.

5. The method of claim 4, wherein the step of stopping the advancement comprises stopping the advancement when the first die holder contacts the first stack side and the second die holder contacts the second stack side.

6. The method of claim 4, wherein the step of stopping the advancement comprises stopping the advancement when the first and second plate assemblies come into contact with one another.

7. The method of claim 3, wherein the first die holder and the first force plate are unitary, and the second die holder and the second force plate are unitary.

8. The method of claim 7, wherein the step of stopping the advancement comprises stopping the advancement when the first die holder contacts the first stack side and the second die holder contacts the second stack side.

9. The method of claim 7, wherein the step of stopping the advancement comprises stopping the advancement when the first and second plate assemblies come into contact with one another.

10. The method of claim 1, further comprising the step of providing an anode tab comprising a first tab portion shaped to fit into a notch and a second tab portion, and wherein:

the step of providing a plurality of anode sheets comprises providing at least one anode sheet having a notch extending into the anode sheet edge in alignment with one of the first cold weld pins of the first planar array and a corresponding axially aligned one of the second cold weld pins of the second planar array; and the positioning step comprises fitting the first tab portion into the notch with the second tab portion extending away from the anode sheet edge, whereby the anode tab is cold welded with the other of the anode sheets during the advancing step.

11. A method of fabricating an electrode stack assembly of an electrolytic capacitor comprising the steps of:

fabricating an anode layer by:

providing the plurality of anode sheets fabricated of a formed valve metal each having first and second sheet sides bounded by an anode sheet edge, stacking the plurality of anode sheets in side-by-side relation in an anode sheet stack having first and second stack sides and a stack height between the first and second stack sides positioning the anode stack in a press fixture comprising a first plate assembly facing the first stack side and a second plate assembly facing the second stack side, the first plate assembly further comprising a plurality of first cold weld dies each having a first cold weld pin extending from a first cold weld die body, the first weld dies mounted in a first planar array with respect to a first force plate for distributing force to the plurality of first cold weld die bodies and such that the first cold weld pins extend toward the first stack side, and the second plate assembly further comprising a plurality of second cold weld dies each having a cold weld pin extending from a cold weld die body, the second cold weld dies mounted in a second planar array with respect to a second force plate for distributing force to the plurality of second cold weld die bodies and such that the second cold weld pins extend toward the second stack side, first and second planar arrays dimensionally aligned to axially align each first cold weld pin of the first planar array with a respective second cold weld pin of the second planar array;

advancing one or both of the first and second plate assemblies toward the first and second stack sides, respectively, to advance the first cold weld pins into the first stack side and the second cold weld pins into the second stack side; and stopping the advancement of the first and second cold weld pins into the first and second stack sides, respectively, when the first and second cold welds are advanced to substantially equal first and second cold weld depths into the respective first and second stack sides, whereby the valve metals of the anode sheets are cold welded together;

providing a cathode layer; and interposing a separator between the anode layer and the cathode layer, the separator carrying an electrolyte.

12. The method of claim 11, wherein:

the first plate assembly comprises a first planar force plate and a substantially planar first die holder having a plurality of die body receptacles formed therein to removably receive the plurality of first cold weld die bodies and fix the first cold weld pins in the first planar array with the first cold weld pins extending substantially equal first pin lengths from the first die holder; and the second plate assembly comprises a second planar force plate and a substantially planar second die holder having a plurality of die body receptacles formed therein to removably receive the plurality of second cold weld die bodies and fix the second cold weld pins in the second planar array with the second cold weld pins extending substantially equal second pin lengths from the second die holder.

13. The method of claim 12, wherein:

the die body receptacles of the first die holder extends through the first die holder, and the first force plate bears against and applies force to the first die bodies located in the first die body receptacles; and the die body receptacles of the second die holder extends through the second die holder, and the first force plate bears against and applies force to the second die bodies located in the second die body receptacles.

14. The method of claim 13, wherein the first die holder and the first force plate are separable from one another, and the second die holder and the second force plate are separable from one another.

15. The method of claim 14, wherein the step of stopping the advancement comprises stopping the advancement when the first die holder contacts the first stack side and the second die holder contacts the second stack side.

16. The method of claim 14, wherein the step of stopping the advancement comprises stopping the advancement when the first and second plate assemblies come into contact with one another.

17. The method of claim 13, wherein the first die holder and the first force plate are unitary, and the second die holder and the second force plate are unitary.

18. The method of claim 17, wherein the step of stopping the advancement comprises stopping the advancement when the first die holder contacts the first stack side and the second die holder contacts the second stack side.

19. The method of claim 17, wherein the step of stopping the advancement comprises stopping the advancement when the first and second plate assemblies come into contact with one another.

20. The method of claim 11, wherein the step of fabricating an anode layer further comprises the step of providing an anode tab comprising a first tab portion shaped to fit into a notch and a second tab portion, and wherein:

the step of providing a plurality of anode sheets comprises providing at least one anode sheet having a notch extending into the anode sheet edge in alignment with one of the first cold weld pins of the first planar array and a corresponding axially aligned one of the second cold weld pins of the second planar array; and the positioning step comprises fitting the first tab portion into the notch with the second tab portion extending away from the anode sheet edge, whereby the anode tab is cold welded with the other of the anode sheets during the advancing step.

* * * * *